(12) United States Patent
Lubenau et al.

(10) Patent No.: US 9,493,738 B2
(45) Date of Patent: Nov. 15, 2016

(54) METHOD FOR PRODUCING HIGH YIELD ATTENUATED SALMONELLA STRAINS

(71) Applicant: Vaximm AG, Basel (CH)

(72) Inventors: Heinz Lubenau, Neustadt an der Weinstrasse (DE); Holger Siede, Ronnenberg (DE); Renate Janssen, Hannover (DE); Marco Springer, Wendlingen (DE)

(73) Assignee: VAXIMM AG, Basel (CH)

( * ) Notice: Subject to any disclaimer, the term of this patent is extended or adjusted under 35 U.S.C. 154(b) by 0 days.

(21) Appl. No.: 14/366,186

(22) PCT Filed: Dec. 21, 2012

(86) PCT No.: PCT/EP2012/005364
§ 371 (c)(1),
(2) Date: Jun. 17, 2014

(87) PCT Pub. No.: WO2013/091898
PCT Pub. Date: Jun. 27, 2013

(65) Prior Publication Data
US 2014/0349274 A1    Nov. 27, 2014

(30) Foreign Application Priority Data
Dec. 22, 2011 (EP) .................................... 11400061

(51) Int. Cl.
| C12Q 3/00 | (2006.01) |
| C12N 1/20 | (2006.01) |
| C07K 14/71 | (2006.01) |
| C12N 1/36 | (2006.01) |
| C12N 1/38 | (2006.01) |
| A61K 39/00 | (2006.01) |
| C12N 15/74 | (2006.01) |

(52) U.S. Cl.
CPC ............ *C12N 1/20* (2013.01); *A61K 39/0011* (2013.01); *C07K 14/71* (2013.01); *C12N 1/36* (2013.01); *C12N 1/38* (2013.01); *C12N 15/74* (2013.01); *C12Q 3/00* (2013.01); *A61K 2039/522* (2013.01)

(58) Field of Classification Search
None
See application file for complete search history.

(56) References Cited

U.S. PATENT DOCUMENTS 7,138,124 B2 * 11/2006 Emery .................. A61K 31/739
424/184.1

FOREIGN PATENT DOCUMENTS

| CN | 1060110 A | 4/1992 |
| CN | 101985610 A | 3/2011 |
| GB | 2 248 241 | 4/1992 |
| JP | 2005-519092 A | 6/2005 |
| WO | WO 03/073995 A2 | 9/2003 |
| WO | WO 03/073995 A3 | 11/2003 |
| WO | WO 2005/026203 A2 | 3/2005 |
| WO | WO 2005/026203 A3 | 4/2006 |
| WO | WO-2010/045620 | 4/2010 |

OTHER PUBLICATIONS

Bumann et al. (Vaccine, 20:845-852, 2002).*
Niethammer, A.G. et al. (2002) "A DNA vaccine against VEGF receptor 2 prevents effective angiogenesis and inhibits tumor growth," Nature Medicine 8(12):1369-1375.
Osorio, M. et al. (2009) "Anthrax Protective Antigen Delivered by *Salmonella enterica* Serovar Typhi Ty21a Protects Mice from a Lethal Anthrax Spore Challenge," Infection and Immunity, 77(4):1475-1482.
Niethammer, A.G. et al. (2012) "Double-blind, placebo-controlled first in human study to investigate an oral vaccine aimed to elicit an immune reaction against the VEGF-Receptor 2 in patients with stage IV and locally advanced pancreatic cancer," BMC Cancer, 12(361):1-8.
International Search Report (ISA/EP) for International Application No. PCT/EP2012/005364, mailed Mar. 25, 2013, 3 pages.
Written Opinion of the International Searching Authority (ISA/EP) for International Application No. PCT/EP2012/005364, mailed Mar. 25, 2013, 9 pages.
First Office Action for Chinese Application No. 201280064144.2, mailed Apr. 21, 2015.
J. Dong et al. (2008), "Recombiant Attentuated *Salmonella* Typhimurium Vaccine SL3261-pcDNA3.1 /flk-1(n1-4) Inhibits Growth of Colorectal Cancer in BALB/c Mice", World Chinese Digest Magazine, 16(2): 163-170, 8 pages.
M. Chen et al. (2006), "Construction of a VEGFR2 DNA Vaccine Aganst Tumor Angiogenesis", Journal of Kunming Medical College, 1:1-5, 6 pages.
C. Wu et al. (2007), "DNA Vaccine Comprising an Attenuated Strain of *Salmonella* as a Carrier Antitumor Against Angio-genesis", Yunnan Pharmaceutics, 28(4): 399-404, 6 pages.
Soini J. et al. (2008), "High cell density media for *Escherichia coli* are generally designed for aerobic cultivations—consequences for large-scale bioprocesses and shake flask cultures", Microbial Cell Factories 2008, 7:26, p. 1-11.
Koma D et al. (2011), "Tips for Biotechnology", Bioengineering, Osaka Municipal Technical Research Institute, 89(4): 195-199.

* cited by examiner

*Primary Examiner* — Brian J Gangle
(74) *Attorney, Agent, or Firm* — Foley & Lardner LLP; Antoinette F. Konski; Melissa J. Brayman

(57) ABSTRACT

This invention relates to a novel method for growing attenuated mutant *Salmonella typhi* strains lacking galactose epimerase activity and harboring a recombinant DNA molecule. The method comprises the step of culturing said *Salmonella typhi* strain without adding glucose to the medium during the fermentation with a starting glucose amount that is depleted before reaching the stationary phase. The invention further relates to attenuated mutant *Salmonella typhi* strains obtainable by said method and to an attenuated mutant *Salmonella typhi* strain harboring a recombinant DNA molecule encoding a VEGF receptor protein for use as a vaccine.

15 Claims, 10 Drawing Sheets

Figure 1

Figure 2:
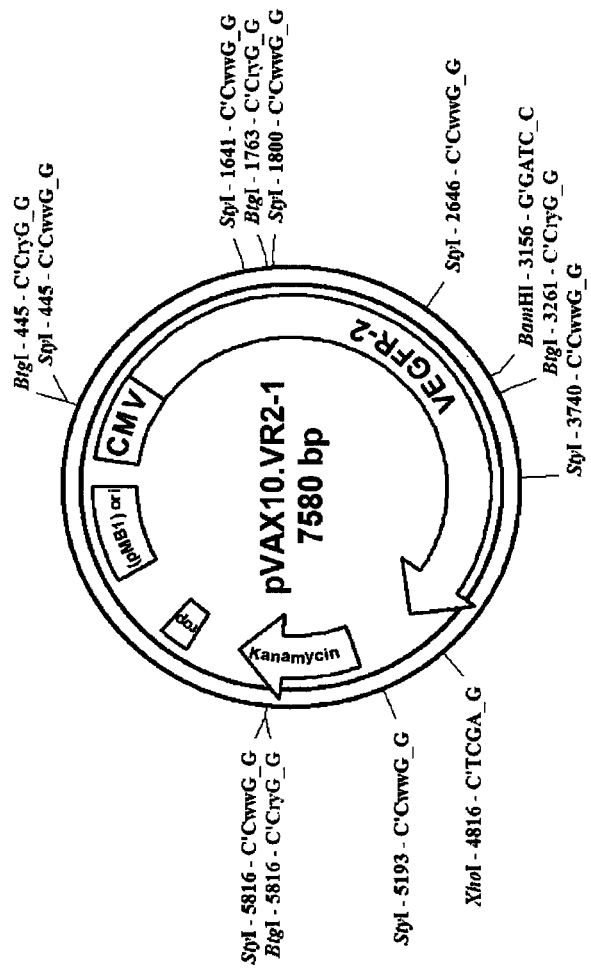
Figure 3:
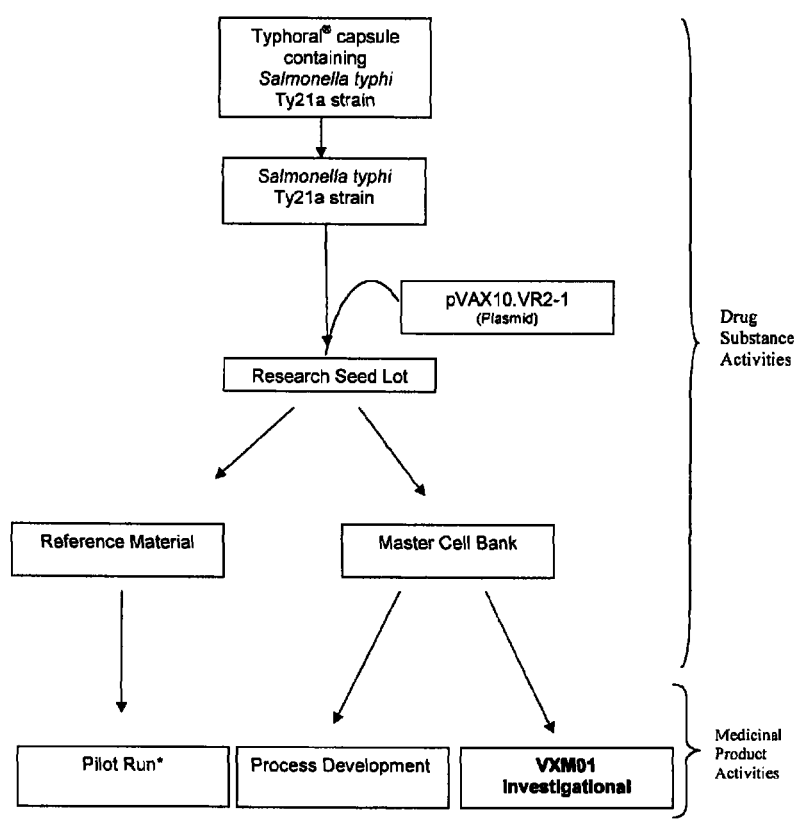
Figure 4:
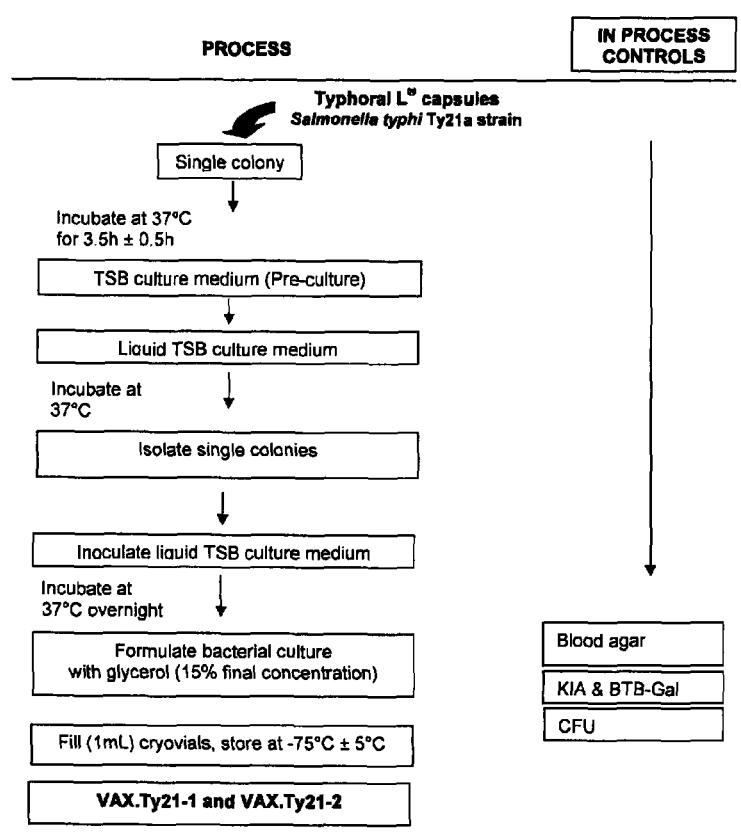

```
              10         20         30         40         50         60
      MQSKVLLAVA LWLCVETRAA SVGLPSVSLD LPRLSIQKDI LTIKANTTLQ ITCRGQRDLD 70         80         90        100        110        120
      WLWPNNQSGS EQRVEVTECS DGLFCKTLTI PKVIGNDTGA YKCFYRETDL ASVIYVYVQD 130        140        150        160        170        180
      YRSPFIASVS DQHGVVYITE NKNKTVVIPC LGSISNLNVS LCARYPEKRF VPDGNRISWD 190        200        210        220        230        240
      SKKGFTIPSY MISYAGMVFC EAKINDESYQ SIMYIVVVVG YRIYDVVLSP SHGIELSVGE 250        260        270        280        290        300
      KLVLNCTART ELNVGIDFNW EYPSSKHQHK KLVNRDLKTQ SGSEMKKFLS TLTIDGVTRS 310        320        330        340        350        360
      DQGLYTCAAS SGLMTKKNST FVRVHEKPFV AFGSGMESLV EATVGERVRI PAKYLGYPPP 370        380        390        400        410        420
      EIKWYKNGIP LESNHTIKAG HVLTIMEVSE RDTGNYTVIL TNPISKEKQS HVVSLVVYVP 430        440        450        460        470        480
      PQIGEKSLIS PVDSYQYGTT QTLTCTVYAI PPPHHIHWYW QLEEECANEP SQAVSVTNPY 490        500        510        520        530        540
      PCEEWRSVED FQGGNKIEVN KNQFALIEGK NKTVSTLVIQ AANVSALYKC EAVNKVGRGE 550        560        570        580        590        600
      RVISFHVTRG PEITLQPDMQ PTEQESVSLW CTADRSTFEN LTWYKLGPQP LPIHVGELPT 610        620        630        640        650        660
      PVCKNLDTLW KLNATMFSNS TNDILIMELK NASLQDQGDY VCLAQDRKTK KRHCVVRQLT 670        680        690        700        710        720
      VLERVAPTIT GNLENQTTSI GESIEVSCTA SGNPPPQIMW FKDNETLVED SGIVLKDGNR.
```

Figure 1 (contd.)

```
          730        740        750        760        770        780
    NLTIRRVRKE DEGLYTCQAC SVLGCAKVEA FFIIEGAQEK TNLEIIILVG TAVIAMFFWL 790        800        810        820        830        840
    LLVIILRTVK RANGGELKTG YLSIVMDPDE LPLDEHCERL PYDASKWEFP RDRLKLGKPL 850        860        870        880        890        900
    GRGAFGQVIE ADAFGIDKTA TCRTVAVKML KEGATHSEHR ALMSELKILI HIGHHLNVVN 910        920        930        940        950        960
    LLGACTKPGG PLMVIVEFCK FGNLSTYLRS KRNEFVPYKT KGARFRQGKD YVGAIPVDLK 970        980        990       1000       1010       1020
    RRLDSITSSQ SSASSGFVEE KSLSDVEEEE APEDLYKDFL TLEHLICYSF QVAKGMEFLA 1030       1040       1050       1060       1070       1080
    SRKCIHRDLA ARNILLSEKN VVKICDFGLA RDIYKDPDYV RKGDARLPLK WMAPETIFDR 1090       1100       1110       1120       1130       1140
    VYTIQSDVWS FGVLLWEIFS LGASPYPGVK IDEEFCRRLK EGTRMRAPDY TTPEMYQTML 1150       1160       1170       1180       1190       1200
    DCWHGEPSQR PTFSELVEHL GNLLQANAQQ DGKDYIVLPI SETLSMEEDS GLSLPTSPVS 1210       1220       1230       1240       1250       1260
    CMEEEEVCDP KFHYDNTAGI SQYLQNSKRK SRPVSVKTFE DIPLEEPEVK VIPDDNQTDS 1270       1280       1290       1300       1310       1320
    GMVLASEELK TLEDRTKLSP SFGGMVPSKS RESVASEGSN QTSGYQSGYH SDDTDTTVYS 1330       1340       1350
    SEEAELLKLI EIGVQTGSTA QILQPDSGTT LSSPPV
```

METHOD FOR PRODUCING HIGH YIELD ATTENUATED *SALMONELLA* STRAINS

CROSS-REFERENCE TO RELATED APPLICATIONS

This application is a national stage application under 35 U.S.C. §371 of International Application No. PCT/EP2012/005364, filed Dec. 21, 2012, which in turn claims priority to European Application No. 11400061.5, filed Dec. 22, 2011, the content of each of which is incorporated herein by reference in their entireties.

FIELD OF THE INVENTION

This invention relates to a novel method for growing attenuated mutant *Salmonella typhi* strains lacking galactose epimerase activity and harboring a recombinant DNA molecule. The method comprises the step of culturing said *Salmonella typhi* strain without adding glucose to the medium during the fermentation with a starting glucose amount that is depleted before reaching the stationary phase. The invention further relates to attenuated mutant *Salmonella typhi* strains obtainable by said method and to an attenuated mutant *Salmonella typhi* strain harboring a recombinant DNA molecule encoding a VEGF receptor protein for use as a vaccine.

BACKGROUND OF THE INVENTION

Among the number of different approaches for vaccine development, live bacterial vaccines are one of the most promising, as they mimic the route of entry of many pathogens and are able to elicit effective humoral and cellular immune responses, at the level of both systemic and mucosal compartments. Live bacterial vaccines can be administered orally or nasally, which offers advantages of simplicity and safety compared to parental administration. Batch preparation costs are relatively low and formulations of live bacterial vaccines show high stability. Attenuation can be accomplished by deletion of various genes, including virulence, regulatory, and metabolic genes.

Attenuated bacterial vaccines can not only be used to induce immunity to their corresponding pathogenic strain, but they can also be modified to deliver one or more heterologous antigens.

Attenuated derivatives of *Salmonella enterica* are attractive as vehicles for the delivery of heterologous antigens to the mammalian immune system because *S. enterica* strains can potentially be delivered via mucosal routes of immunization and have the ability to invade host tissues and persist, while continuing to produce a heterologous antigen. Furthermore, *Salmonella* strains elicit strong humoral and cellular immune responses, at the level of both systemic and mucosal compartments.

Several *Salmonella typhimurium* strains attenuated by aro mutations have been shown to be safe and effective delivery vehicles for heterologous antigens in animal models.

Approaches of delivering DNA constructs encoding heterologous antigens, in particular VEGF receptor proteins, via live attenuated *Salmonella typhimurium* strains into mouse target cells are described in WO 03/073995. Niethammer et al., (Nature Medicine 2002, 8(12), 1369) demonstrated that the attenuated *S. typhimurium* aroA strain SL7207 harboring an expression vector encoding the murine vascular endothelial growth factor receptor 2 (VEGFR-2 or FLK-1), which is essential for tumor angiogenesis, is functional as a cancer vaccine.

There is however only one attenuated *Salmonella enterica* serovar strain, namely *Salmonella enterica* serovar typhi Ty21a (short: *S. typhi* Ty21a), which has been accepted for use in humans.

This well-tolerated, live oral vaccine against typhoid fever was derived by chemical mutagenesis of the wild-type virulent bacterial isolate *S. typhi* Ty2 and harbors a loss-of-function mutation in the galE gene, as well as other less defined mutations. It has been licensed as typhoid vaccine in many countries after it was shown to be efficacious and safe in field trials.

There is a strong demand for live attenuated bacterial vectors as delivery vehicles for heterologous antigens—especially cancer antigens—that are safe for use in humans. The provision of such an attenuated bacterial vector as DNA vaccine also calls for the efficient, high-yield cultivation of the attenuated bacterial strain transformed with said heterologous antigen DNA. Transformation of bacterial strains with recombinant DNA constructs often results in decreased cell growth. Thus, it is often necessary to improve the preferably large-scale cultivation process to obtain high yields of viable and functionally active cells.

OBJECTS OF THE INVENTION

It was an object of the present invention to improve the methods of the prior art for growing attenuated mutants strains of *Salmonella typhi*. In particular, it was an object of the present invention to develop an efficient cultivation method for obtaining high yields of viable bacterial cells harboring a recombinant DNA molecule encoding a heterologous antigen. Such a method and attenuated mutant strains of *Salmonella typhi* obtainable by such a method would serve to satisfy the great need for safe attenuated *Salmonella* strains as DNA vaccines for use in humans. Such a method would be particularly suitable for the commercial large-scale production of DNA vaccines based on attenuated *Salmonella* strains.

SUMMARY OF THE INVENTION

Surprisingly, it has been found that the cell yield of an attenuated *Salmonella typhi* strain lacking galactose epimerase activity can be remarkably increased, if the amount of glucose in the medium is reduced to zero before reaching the stationary phase. The inventors have shown that glucose addition to the medium during fermentation does not result in higher cell mass/higher OD values. On the contrary, omitting glucose addition during the cultivation of the attenuated *Salmonella* strain yields in optical densities of about 6 to about 8 at the onset of the stationary phase of cell growth, whereas identical culturing at a glucose level of about 1 to about 4 g/I, preferably of about 2 to about 3 g/I (e.g. achieved by sequentially pulsing the medium with glucose) results in optical densities of only about 3 to about 5.5.

The method for growing an attenuated mutant strain of *Salmonella typhi* according to the invention further yields cells of different morphology as compared to cells cultivated with glucose. *Salmonella typhi* cells grown without glucose are smaller and shorter than cells cultivated with glucose. However, these morphologically different cells, like the cells grown in a glucose containing medium, are fully biologically active and do not show any tendency for cell lysis.

The increase in cell yield obtained by omitting glucose-addition during cultivation according to the method of the present invention is observed regardless of whether the selected attenuated mutant strain of *Salmonella typhi* harbors a recombinant DNA molecule encoding a heterologous antigen (such as pcDNA3.1-FLK1, or a plasmid derived thereof, like pVAX10.VR2-1) or not (the empty attenuated strain).

Thus, in one aspect, the present invention relates to a method for growing an attenuated mutant strain of *Salmonella typhi* lacking galactose epimerase activity and comprising at least one copy of a recombinant DNA molecule comprising an expression cassette, comprising the step of culturing the strain in a buffered medium comprising peptone at approximately neutral starting pH value at fermentation scale, wherein the amount of glucose in the medium during the fermentations is adjusted such that the amount of glucose is reduced to zero before reaching the stationary phase.

In a particular embodiment, no glucose is added to the medium during the fermentation and the starting amount of glucose is depleted before reaching the stationary phase.

In a particular embodiment, said attenuated mutant strain of *Salmonella typhi* is *Salmonella typhi* Ty21a.

In a particular embodiment, the expression cassette is a eukaryotic expression cassette. In a particular embodiment, the expression cassette encodes a VEGF receptor protein. In a particular embodiment, the VEGF receptor protein is selected from the group consisting of human VEGFR-2 and a homolog thereof that shares at least about 80% homology therewith. In a preferred embodiment, human VEGFR-2 has the amino acid sequence as found in SEQ ID NO 1.

In a particular embodiment, the buffered medium comprises peptone of non-animal origin. In a preferred embodiment, said buffered medium is Tryptic Soy Broth (TSB) of non-animal origin.

In a particular embodiment, the volume of the medium is at least about 10 l, more particularly from about 10 l to about 10.000 l, more particularly from about 30 l to about 1.000 l, most particularly from about 100 Ito about 5001.

In a particular embodiment, the starting glucose concentration corresponds to that of bacterial minimal medium or less, particularly the starting glucose concentration is from about 0 g/l to about 4 g/l.

In a particular embodiment, the starting pH value is from about 5 to less than about 9, particularly from about 6 to about 8, more particularly from about 6.5 to about 7.5.

In a particular embodiment, the pH value is adjusted during said culturing to a pH value of about 6 to about 8, particularly to a pH value of about 6.5 to about 7.5.

In a particular embodiment, the progress of growth is determined by measuring the optical density (OD), particularly by in-situ monitoring of the optical density of the culture or by taking samples and measuring the optical density of the samples.

In another particular embodiment, the progress of growth is determined by measuring the cell density, particularly microscopically or by measuring the electrical resistance, or by flow cytometry.

In another particular embodiment, the progress of growth is determined by measuring the colony forming units (CFU) value by taking samples and plating on agar plates.

In a particular embodiment, the cells are harvested before reaching an optical density of about 6, particularly at an optical density of about 5 to about 6.

In a particular embodiment, the attenuated mutant strain of *Salmonella typhi* is *Salmonella typhi* Ty21a and the recombinant DNA molecule comprises the kanamycin resistance gene, the pMB1 ori, and a eukaryotic expression cassette encoding human VEGFR-2, under the control of the CMV promoter. In a particular embodiment, human VEGFR-2 has the nucleic acid sequence as found in SEQ ID NO 2.

In another aspect, the present invention relates to an attenuated mutant strain of *Salmonella typhi* lacking galactose epimerase activity and comprising at least one copy of a recombinant DNA molecule comprising an expression cassette, obtainable by a method for growing the strain, comprising the step of culturing the strain in a buffered medium comprising peptone at about neutral starting pH value at fermentation scale, wherein the amount of glucose in the medium during the fermentations is adjusted such that the amount of glucose is reduced to zero before reaching the stationary phase.

In a particular embodiment, no glucose is added to the medium during the fermentation and the starting amount of glucose is depleted before reaching the stationary phase.

In a particular embodiment, the expression cassette is a eukaryotic expression cassette encoding a VEGF receptor protein. In a particular embodiment, the eukaryotic expression cassette encodes a VEGF receptor protein selected from the group consisting of human VEGFR-2 and a homolog thereof that shares at least about 80% homology therewith. In a particular embodiment, human VEGFR-2 has the amino acid sequence as found in SEQ ID NO 1.

In a particular embodiment, the attenuated mutant strain is *Salmonella typhi* Ty21a and the recombinant DNA molecule comprises the kanamycin resistance gene, the pMB1 ori, and a eukaryotic expression cassette encoding human VEGFR-2 under the control of the CMV promoter. In a particular embodiment, human VEGFR-2 has the nucleic acid sequence as found in SEQ ID NO 2.

In yet another aspect, the present invention relates to an attenuated mutant strain of *Salmonella typhi* Ty21a comprising at least one copy of a recombinant DNA molecule comprising a eukaryotic expression cassette encoding a VEGF receptor protein for use as a vaccine.

In certain embodiments, the VEGF receptor protein is selected from the group consisting of human VEGFR-2 and a homolog thereof that shares at least about 80% homology therewith.

In a preferred embodiment, the human VEGFR-2 has the amino acid sequence as found in SEQ ID NO 1.

The fact that higher cell yields of attenuated mutant strains of *Salmonella typhi* can be obtained by the method according to the invention, is of importance with respect to the safe and economic manufacture of a commercial DNA vaccine based on an attenuated *Salmonella* strain, such as the approved *Salmonella typhi* Ty21a strain. *Salmonella typhi* Ty21a carrying a recombinant DNA molecule encoding a heterologous antigen, such as the expression plasmid pVAX10.VR2-1, can thus be cultured in higher yields, resulting in higher yields of the DNA vaccine for use in humans. This is also in compliance with the strong safety rules which must be applied when manufacturing and cultivating *Salmonella*, even in an attenuated version.

DETAILED DESCRIPTION OF THE INVENTION

The present invention may be understood more readily by reference to the following detailed description of the invention and the examples included therein.

1) *Salmonella typhi* Including Wild-Type *Salmonella typhi* Ty2 and Attenuated *Salmonella typhi* Ty21a Within the subject method any attenuated *Salmonella typhi* strain may be used. The attenuated *S. typhi* Ty21a strain is the active component of TYPHORAL L®, also known as VIVOTIF® (a typhoid oral vaccine comprising Ty21a manufactured by Berna Biotech Ltd., a Crucell Company, Switzerland). It is currently the only licensed live oral vaccine against typhoid fever. This vaccine is licensed in more than 40 countries. The Marketing Authorization number of TYPHORAL L® (typhoid oral vaccine comprising Ty21a) is PL 15747/0001 dated 16 Dec. 1996. One dose of vaccine contains at least $2 \times 10^9$ viable *S. typhi* Ty21a colony forming units and at least $5 \times 10^9$ non-viable *S. typhi* Ty21a cells. The vaccine strain is grown in fermenters under controlled conditions in medium containing a digest of yeast extract, an acid digest of casein, glucose and galactose.

One of the biochemical properties of the *Salmonella typhi* Ty21a bacterial strain, as used according to this invention, is its inability to metabolize galactose. The recombinant attenuated bacterial strain is also not able to reduce sulfate to sulfide which differentiates it from the wild-type *Salmonella typhi* Ty2 strain. In regards to the serological characteristics of *Salmonella typhi* Ty21a strain, it contains the 09-antigen which is a polysaccharide of the outer membrane of the bacteria and lacks the 05-antigen which is in turn a characteristic component of *Salmonella typhi* Ty2. Again, this serological characteristic supports the rationale for including the appropriate test in the panel of identity tests for batch release.

In a particular embodiment, the attenuated mutant strain of *Salmonella typhi* grown by the method according to the invention is *Salmonella typhi* Ty21a carrying at least one copy of a plasmid DNA, pVAX10.VR2-1, encoding a eukaryotic expression cassette of the human Vascular Endothelial Growth Factor Receptor 2 (VEGFR-2). This attenuated mutant strain is designated VXM01 and can be used as an oral cancer vaccine.

According to the invention, the attenuated *Salmonella typhi* Ty21a strain functions as the bacterial carrier of the plasmid DNA encoding the heterologous antigen Vascular Endothelial Growth Factor Receptor 2 (VEGFR-2), in the oral delivery of the DNA vaccine designated VXM01.

Delivery of vaccines based on plasmid DNA technology results in a broad spectrum of both mucosal and systemic immune responses. Live replicating vectors produce their own immunomodulatory factors such as lipopolysaccharides (LPS) in situ which may constitute an advantage over other forms of administration such as microencapsulation. Moreover, the use of the natural route of entry proves to be of benefit since many bacteria, like *Salmonella*, egress from the gut lumen via the M cells of Peyer's patches and migrate eventually into the lymph nodes and spleen, thus allowing targeting of vaccines to inductive sites of the immune system. The vaccine strain of *Salmonella typhi, Ty*21a, has been demonstrated to-date to have an excellent safety profile. Upon exit from the gut lumen via the M cells, the bacteria are taken up by phagocytic cells, such as macrophages and dendritic cells. These cells are activated by the pathogen and start to differentiate, and probably migrate, into the lymph nodes and spleen. Due to their attenuating mutations, bacteria of the *S. typhi* Ty21 strain are not able to persist in these phagocytic cells but die at this time point. There is no data available to-date indicating that *S. typhi* Ty21a is able to enter the bloodstream systemically. The live attenuated *Salmonella typhi* Ty21a vaccine strain thus allows specific targeting of the immune system while exhibiting an excellent safety profile.

Live attenuated bacterial carriers that carry DNA encoding target antigens, can be used as vehicles for the oral delivery of these antigens. Live replicating vectors produce, in situ, their own immunomodulatory factors, such as lipopolysaccharides (LPS), which also constitutes an advantage over other forms of vaccine administration, like microencapsulation.

Genetic immunization might be advantageous over conventional vaccination. The target DNA can be detected for a considerable period of time thus acting as a depot of the antigen. Sequence motifs in some plasmids, like GpC islands, are immunostimulatory and can function as adjuvants furthered by the immunostimulation due to LPS and other bacterial components.

As indicated above, the recombinant *Salmonella* bacteria are taken up by phagocytic cells upon exit from the gut lumen via the M cells. These phagocytic cells are activated by the pathogen and start to differentiate, and probably migrate, into the lymph nodes and spleen. During this period, the bacteria die due to their attenuated mutation and release the plasmid-based eukaryotic expression vectors followed by a transfer of the plasmids into the cytosol, either via a specific transport system or by endosomal leakage. Finally, the vector enters the nucleus, where it is transcribed, leading to antigen expression in the cytosol of the host cell. Specific cytotoxic T cells against the heterologous antigen, preferably human VEGFR-2, are induced by the activated antigen presenting cells (APCs).

In a particular embodiment, the recombinant DNA molecule carried by the *Salmonella typhi* Ty21a strain is a plasmid DNA, pVAX10.VR2-1 (7.58 kb), containing a eukaryotic Human Cytomegalovirus (CMV) immediate-early promoter, to ensure efficient transcription of the VEGFR-2 protein in the host cell, and a prokaryotic origin of replication (ori), to ensure multiplication within the bacterial host. The vector pcDNA3 is commercially available (Invitrogen) and was modified to comply with regulatory requirements whereby the sequences not necessary for replication in *E. coli* or for expression of the recombinant proteins in mammalian cells were removed to limit the DNA sequences with possible homology to the human genome and to minimize the possibility of chromosomal integration. Furthermore, the kanamycin resistance gene substituted the ampicillin resistant gene. For the attenuated mutant *Salmonella typhi* strain VXM01 produced according to the method of this invention, the high copy pUC origin of the pVAX1-Flk-1 plasmid was replaced by the low copy origin of replication of pBR322 in the pVAX10.VR2-1. The low copy modification was made in order to reduce the metabolic burden and to make the construct more stable. Details of the plasmid pVAX10.VR2-1 construct are depicted in FIG. 2.

2) Vascular Endothelial Growth Factor Receptor:

Vascular Endothelial Growth Factor VEGF (Kd 75-760 µM) is a member of a family of six structurally related proteins (VEGF-A [also known as VEGF], -B, -C, -D, -E and PLGF [placental growth factor, also known as PGF or PIGF-2]) that regulates the growth and differentiation of multiple components of the vascular system, especially blood and lymph vessels. The role of VEGF in angiogenesis appears to be mediated through the interaction of this protein with VEGFR-2. VEGFR-2, also known as kinase-insert-domain-containing receptor (KDR), is a 1356 amino acid long, 200-230 kDa molecular weight high-affinity receptor for VEGF, as well as for VEGF-C and VEGF-D. Identified in humans through the screening of endothelial cDNA for tyrosine kinase receptors, VEGFR-2 shares 85% sequence identity with the previously discovered murine VEGFR-2, also known as fetal liver kinase 1 (Flk-1). VEGFR-2 is normally expressed in endothelial and hematopoietic precursors, as well as in endothelial cells, nascent hematopoietic stem cells and the umbilical cord stroma. However, in quiescent adult vasculature, VEGFR-2 mRNA appears to be down regulated.

The extracellular domain of VEGFR-2 contains 18 potential N-linked glycosylation sites. VEGFR-2 is initially synthesized as a 150 kDa protein and rapidly glycosylated to a 200 kDa intermediate form, and then further glycosylated at a slower rate to a mature 230 kDa protein which is expressed on the cell surface.

The amino acid sequence of the human VEGFR-2 encoding cDNA sequence cloned into the pVAX10.VR2-1 plasmid is presented in FIG. 1.

tion that omitting glucose-addition during cultivation of attenuated mutant strains of *Salmonella typhi* optionally harboring a recombinant DNA molecule encoding a heterologous antigen leads to an increased cell growth compared to cultivation with glucose-addition is very surprising and suggests that specific metabolic pathways in the bacterial cells are triggered by the absence of glucose. The effect described can also be observed, if the TSB or TSB-like medium does not contain any glucose at the beginning of the cultivation process. Therefore, the method according to the invention has, apart from higher cell yields and thus higher yields of the final DNA vaccine, the further advantage of being cheaper and simpler by rendering the glucose feeding steps during fermentation unnecessary.

The manufacturing process of the attenuated mutant strain of *Salmonella typhi* Ty21a as carried out according to the invention is exemplarily described in the following Table 1:

Cells I (*Salmonella Typhi* Ty21a, WT) or Cells II (*Salmonella Typhi* Ty21a-pVAX10.VR2-1

↓

2 × 500 ml TSB + kanamycin (500 µL)

($OD_{600}$ > 0.3)

↓

10 × 1000 ml TSB + kanamycin (75 mL)

($OD_{600}$ ≥ 0.5)

100 L Fermentation volume
TSB + 0.001% galactose
30° C.
Airflow 100 L/min (1 vvm)
pressure not controlled
pH 7.0 controlled with NaOH
foam controlled (Corning)
$pO_2$ ≥ 40% regulated by stirrer
stirrer minimum 200 rpm
no glucose feeding
Final $OD_{600\ nm}$ (end of exponential growth phase)
Cooling to at least 25° C. before harvest
Cross flow filtration
10 fold concentration
10 fold buffer exchange on diafiltration with 15%
sucrose, 0.45% ascorbate solution pH 7.2, followed by
further concentration to 1/20 vol. of original harvest
Store at 2-8° C. until filling about 24 hours 3) Manufacturing of Empty and Engineered *Salmonella typhi* Ty21a The manufacturing process of the attenuated mutant strain of *Salmonella typhi* as carried out according to the invention comprises culturing the attenuated mutant strain of *Salmonella typhi* in medium which comprises peptone as a source for amino acids and peptides. Media suitable for the method of the present invention include, but are not limited to, standard TSB medium as well as TSB medium of non-animal origin. Both standard TSB as well as TSB of non-animal origin comprise 2.5 g/l glucose. Usually, the starting glucose amount in TSB, or TSB-like medium is more or less completely consumed after 3-5 h of cultivation of an attenuated *Salmonella typhi* strain, and must be substituted by fresh glucose every 3-5 h in order to sustain a more or less constant glucose level in the culture medium. The observa- In more detail: The cultures (TSB medium plus 25 µg/ml kanamycin) are inoculated each with different samples of the *salmonella* strains (empty Ty21a and recombinant Ty21a (pVAX10.VR2-1). In the production cell samples TSB medium is used containing 2.5-3.0 g/l glucose, preferably 2.5 g/l. In one control medium glucose is omitted. Furthermore, the medium contains kanamycin, preferably 25 µg/ml. The cultures are incubated at 30° C.±2° C. with shaking until an Optical Density $OD_{600nm}$>0.1 is reached. Further details are described in the Example section.

In-process controls for the first and second pre-culture steps, at the completion of the incubation times, includes analysis of bacterial growth by measuring $OD_{600nm}$, pH and CFU/ml as well as, if applicable, determination of plasmid stability (PST) and bacterial examination. The latter analysis is based on a blood agar assay for determining hemolytic reactions of fastidious pathogenic microorganisms. The CFU value is assessed before and after the cross flow filtration (CFF). Upon formulation of the final bacterial concentrate, CFU and refractive index were measured on the formulation with the lowest bacterial concentration.

The method according to the invention, wherein glucose feeding is omitted, is less labor intensive and more efficient, resulting in higher cell yields.

4) Influence of Glucose Feeding During Culturing Cells

Growth of cells of empty and engineered *Salmonella typhi* Ty21a was tested in a TSB or TSB-like medium by culturing the cells between 0 and 30 hours at 25-35° C., preferably 30° C. and a pH between 6.5 and 7.5, preferably 7.0. Growth was measured in OD or in CFU/ml (colony forming units).

The results of these experiments show, that glucose addition does not result in higher OD-values/cell mass yields of the wild type strain despite of glucose consumption. In contrast, flasks without glucose addition reached higher OD values (6 for preculture 1, 8 for preculture 2). Approx. 1 h after glucose addition OD remained static (or even slightly declined) compared to growth without glucose addition. On repeated pulses glucose consumption declined, no additional/additive effect on growth was observed. pH values were also monitored during fermentation, and in some experiments adjusted to the starting pH value, if shifts could be observed.

Figure 8:
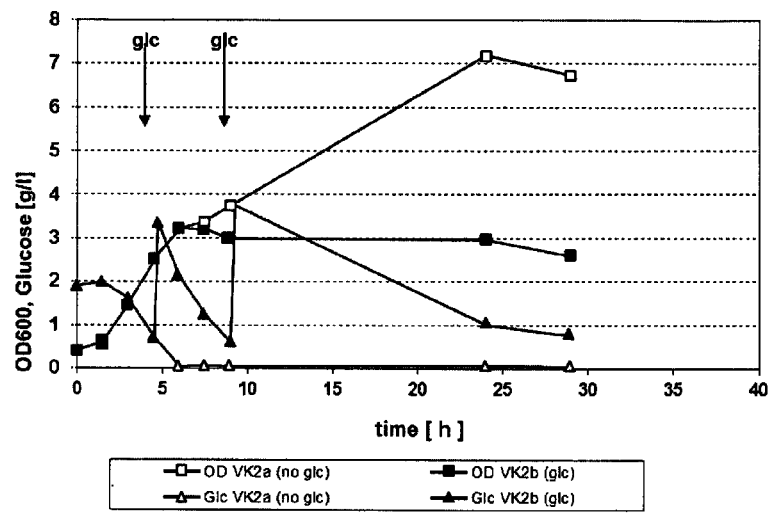
Figure 9:
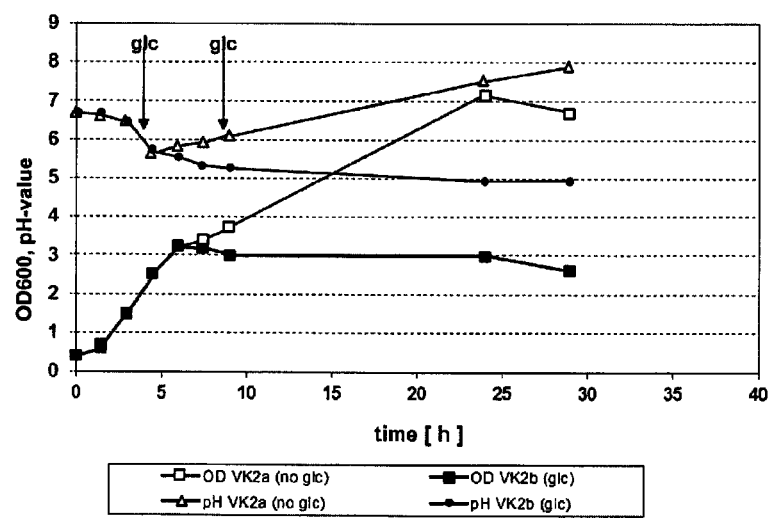

Without glucose addition a shift of pH to alkaline was observed after depletion of glucose, while with glucose pulse pH-value dropped (compare FIG. 8 for preculture 1 and FIG. 9 for preculture 2). Phenomena were observed in all precultures used, indicating no influence of generation number. Glucose pulsing was done 1-5 times (preferably 1-3 times) during an average culturing time of maximum 30 h. Usually, after approximately 5-15 hours cell growth entered the stationary phase after the exponential phase, depending on the starting conditions of the cell culture. If a preculture grown with glucose pulse was inoculated into fresh medium the same growth characteristics (higher OD values/pH shift to alkaline without glucose addition) were observed.

By omitting glucose feeding in the growth phase or even in the starting medium from the beginning, a shift of the pH values to alkaline (from ca. 7 to ca. 8) can be observed, although the medium system is buffered. It might be favorable to adjust the pH value during cell growth to the original starting pH of ca. 7.0.

Results indicated that glucose concentrations above a comparably low limit (approx. 2.5 g/l) trigger a reversible change in (glucose) metabolism. Without wishing to be bound by any theory, it is presumed that a substance, not yet identified, is then secreted into the medium which inhibits further growth, even if glucose declines again below trigger level. After inoculation in new medium this substance is diluted to a concentration beneath effectiveness. Very similar results can be obtained, if the starting medium does not contain any glucose.

Figure 12:
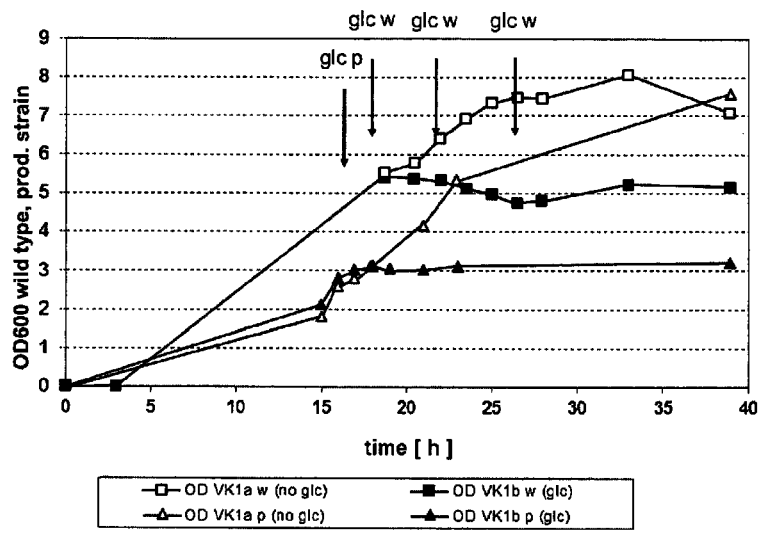
Figure 13:
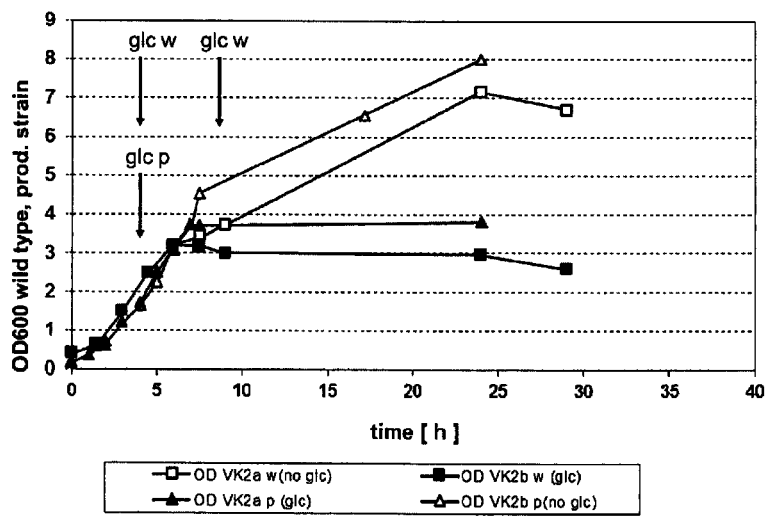

Interestingly the same results can be obtained not only with the empty *Salmonella typhi* Ty21a but also with the engineered strain *Salmonella typhi* Ty21a-pVAX10.VR2-1 (VXM01), indicating that the surprising effect is not influenced by the artificially engineered bacterial construct. However, as it can be seen from FIG. 12, the cell growth of the engineered bacterium without glucose feeding, is—as expected—slower than of the wild-type strain, but finally can gain the same high optical density values (OD 7-8) as compared with the wild-type strain, whereas the engineered *Salmonella* strain cultured in the presence of glucose by glucose pulsing does never gain these high optical density values and stops, as a rule at a cell density of OD 3 or less.

Both the empty as well as the engineered *S. typhi* Ty21a strain show comparable growth characteristics regarding growth with and without glucose addition.

To sum up, the results of the invention as described above and in the following show with both strains, that glucose addition does not result in higher OD-values/cell mass yields. In contrast, flasks without glucose addition reached higher OD values. Without glucose addition a shift of pH to alkaline is observed after depletion of glucose while with glucose pulse pH-value drops. One effect of glucose concentration dependent change in metabolism during cultivating of *Salmonella typhi* Ty21a consists presumably in excretion of an inhibitory substance into growth medium, which is not known so far.

In one aspect, the present invention relates to a method for growing an attenuated mutant strain of *Salmonella typhi* lacking galactose epimerase activity and comprising at least one copy of a recombinant DNA molecule comprising an expression cassette, comprising the step of culturing the strain in a buffered medium comprising peptone at approximately neutral starting pH value at fermentation scale, wherein the amount of glucose in the medium during the fermentations is adjusted such that the amount of glucose is reduced to zero before reaching the stationary phase.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components or groups thereof. The term "comprising" thus includes the more restrictive terms "consisting of" and "essentially consisting of".

In the context of the present invention, the term "about" or "approximately" means within 20%, alternatively within 10%, including within 5% of a given value or range. Alternatively, especially in biological systems, the term "about" means within about a log (i.e. an order of magnitude), including within a factor of two of a given value.

In the context of the present invention, the terms "growing" and "culturing" are used synonymously and refer to propagation of microorganisms in media conductive to their growth.

In the context of the present invention, the term "fermentation" refers to large-scale culturing of microorganisms, typically performed in a fermenter, i.e. an apparatus that maintains optimal conditions for the growth of said microorganisms, for the high-yield production of a desired microbial product, including metabolites and the microorganisms themselves.

In the context of the present invention, the term "attenuated" refers to a bacterial strain of reduced virulence compared to the parental bacterial strain, not harboring the attenuating mutation. Attenuated bacterial strains have preferably lost their virulence but retained their ability to induce protective immunity. Attenuated bacteria may be found naturally or they may be produced in the laboratory, for example by adaptation to a new medium or cell culture or they may be produced by recombinant DNA technology.

In the context of the present invention, the term "mutant strain" refers to a bacterial strain harboring a mutation in its genome. In this context, the term "mutation" refers to a change in a nucleic acid sequence, including point mutations, insertions, deletions, translocations and inversions.

In the context of the present invention, the term "recombinant DNA molecule" refers to an engineered DNA construct, preferably composed of DNA pieces of different origin. The recombinant DNA molecule can be a linear nucleic acid, or preferably, a circular recombinant DNA plasmid generated by introducing an open reading frame of interest into an expression vector plasmid. The open reading frame is preferably a heterologous antigen. The heterologous antigen is preferably a cancer antigen. The cancer antigen is preferably a VEGF receptor protein. In the context of the present invention, the term "heterologous antigen" refers to an antigen derived from a species other than *Salmonella typhi*.

In the context of the present invention, the term "expression cassette" refers to a nucleic acid unit comprising at least one gene under the control of regulatory sequences controlling its expression. Expression cassettes comprised in the attenuated mutant strain of *Salmonella typhi* can preferably mediate transcription of the included open reading frame in target cells. Expression cassettes typically comprise a promoter, at least one open reading frame and a transcription termination signal.

In the context of the present invention, the term "peptone" refers to a mixture of cleavage products comprising amino acids and peptides produced by hydrolysis of protein-containing materials, for example by partial acid or enzymatic hydrolysis of native protein mixtures.

In the context of the present invention, the term "approximately neutral pH value" refers to a pH value of from about 5 to about 9, preferably from about 6 to about 8, more preferably from about 6.5 to about 7.5, most preferably about 7.0.

Media suitable for the method of the present invention include, but are not limited to, standard TSB medium as well as TSB medium of non-animal origin. Standard TSB medium known in the art is comprised of pancreatic casein peptone, soybean meal peptone, di-potassium hydrogen phosphate (buffer), sodium chloride, and glucose (=dextrose) as energy source in a starting concentration of 2.5 g/l. An example of suitable TSB medium of non-animal origin is CASO Bouillon of non-animal origin comprised of non-animal derived peptone, di-potassium hydrogen phosphate (buffer), sodium chloride, and glucose in a starting concentration of 2.5 g/l.

In the context of the present invention, the term "stationary phase" refers to the stage of bacterial growth after the exponential or logarithmic phase, wherein the cell density in the growth medium remains approximately constant. The term "before reaching the stationary phase" thus refers to any time point before the stationary phase and includes the lag phase (i.e. the first phase of bacterial growth during which the bacteria adapt to the growth conditions) and the exponential phase. It was surprisingly found that cultivation of attenuated mutant strains of *Salmonella typhi* according to the method of the present invention prolongs the exponential growth phase. When growing the attenuated mutant strain *Salmonella typhi* Ty21a with a starting glucose amount that is depleted during the exponential growth phase without addition of glucose during the fermentation process, the stationary phase is reached not earlier than after 9 hours of culturing, preferably after 9 to 20 hours of culturing, more preferably after 9 to 15 hours after culturing, most preferably after 9 to 12 hours after culturing.

In a particular embodiment, no glucose is added to the medium during the fermentation and the starting amount of glucose is depleted before reaching the stationary phase. It is however also within the subject method of growing an attenuated mutant strain of *Salmonella typhi*, to add glucose, as long as the amount of glucose is reduced to zero before reaching the stationary phase.

In the context of the present invention, the term "glucose is depleted" means that the starting amount of glucose in the medium is consumed (i.e. taken up and metabolized) by the bacteria.

In a particular embodiment, the attenuated mutant strain of *Salmonella typhi* is *Salmonella typhi* Ty21a.

In a particular embodiment, the expression cassette is a eukaryotic expression cassette. It has been shown that the amount of heterologous antigen required to induce an adequate immune response may be toxic for the bacterium and result in cell death, over-attenuation or loss of expression of the heterologous antigen. Using a eukaryotic expression cassette that is not expressed in the bacterial vector but only in the target cell overcomes this toxicity problem.

In the context of the present invention, the term "eukaryotic expression cassette" refers to an expression cassette which allows for expression of the open reading frame in a eukaryotic cell. A eukaryotic expression cassette comprises regulatory sequences that are able to control the expression of an open reading frame in a eukaryotic cell, preferably a promoter and a polyadenylation signal. Promoters and polyadenylation signals included in the recombinant DNA molecules comprised by the *Salmonella typhi* strain for use as a vaccine of the present invention are preferably selected to be functional within the cells of the subject to be immunized. Examples of promoters useful in the attenuated mutant *Salmonella typhi* strain of the present invention, especially in the production of a DNA vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, Cytomegalovirus (CMV) such as the CMV immediate early promoter, Epstein Barr Virus (EBV), Rouse Sarcoma Virus (RSV) as well as promoters from human genes such as human actin, human myosin, human hemoglobin, human muscle creatine, and human metallothionein. In a particular embodiment, the eukaryotic expression cassette contains the CMV promoter. In the context of the present invention, the term "CMV promoter" refers to the immediate-early cytomegalovirus promoter.

Examples of suitable polyadenylation signals, especially for the production of a DNA vaccine for humans, include but are not limited to the BGH polyadenylation site, SV40 polyadenylation signals and LTR polyadenylation signals. In a particular embodiment, the eukaryotic expression cassette included in the recombinant DNA molecule comprised by the attenuated mutant strain of *Salmonella typhi* of the present invention comprises the BGH polyadenylation site.

In addition to the regulatory elements required for expression of a heterologous gene, such as a heterologous antigen, like promoters and polyadenylation signals, other elements can also be included in the recombinant DNA molecule. Such additional elements include enhancers. The enhancer can be, for example, the enhancer of human actin, human myosin, human hemoglobin, human muscle creatine and viral enhancers such as those from CMV, RSV and EBV.

Regulatory sequences and codons are generally species dependent, so in order to maximize protein production, the regulatory sequences and codons are preferably selected to be effective in the species to be immunized. The person skilled in the art can produce recombinant DNA molecules that are functional in a given subject species.

In a particular embodiment, the expression cassette encodes a VEGF receptor protein.

VEGF receptor proteins are endothelial cell-specific receptor-tyrosine kinases that can be bound by the ligand vascular endothelial growth factor (VEGF) which causes them to dimerize and become activated through transphosphorylation. There are three main subtypes of VEGFR, VEGFR-1 (or FLT1), VEGFR-2 (or KDR, FLK1) and VEGFR-3 (or FLT4). VEGFR-2 appears to mediate almost all of the known cellular responses to VEGF. Membrane-bound VEGF receptors have an extracellular portion consisting of 7 immunoglobulin-like domains, a single transmembrane spanning region and an intracellular portion containing a split tyrosine-kinase domain. VEGFR transcripts give also rise to alternative splice variants that encode soluble VEGF receptor proteins. The VEGF family of growth factors encompasses 6 family members, VEGF-A through E and PGF. In a preferred embodiment, the eukaryotic expression cassette encodes a VEGF receptor protein selected from the group consisting of human VEGFR-2 and a homolog thereof that shares at least about 80% homology therewith.

In the context of the present invention, the term "homolog" of human VEGFR-2 refers to a VEGF receptor protein that differs in the amino acid sequence and/or the nucleic acid sequence encoding the amino acid sequence of human VEGFR-2. The homolog of human VEGFR-2 may be of natural origin, e.g. a homolog of VEGFR-2 of a different species, or an engineered VEGFR-2 homolog. It is known that the usage of codons is different between species. Thus, when expressing a heterologous protein in a target cell, it may be necessary, or at least helpful, to adapt the nucleic acid sequence to the codon usage of the target cell. Methods for designing and constructing homologs of VEGF receptor proteins are well known to anyone of ordinary skill in the art.

A VEGFR-2 homolog may contain one or more mutations comprising an addition, a deletion and/or a substitution of one or more amino acids. According to the teaching of the present invention, said deleted, added and/or substituted amino acids may be consecutive amino acids or may be interspersed over the length of the amino acid sequence of the functional VEGFR-2 homolog. According to the teaching of the present invention, any number of amino acids may be added, deleted, and/or substitutes, as long as the homolog and human VEGFR-2 share at least about 80% homology. In particular embodiments, the homolog of human VEGFR-2 has a sequence homology of at least about 80%, at least about 85%, at least about 90%, or most particularly of at least about 95% and a sequence identity of at least about 60%, at least about 65%, at least about 70% and most particularly of at least about 75%. Methods and algorithms for determining sequence identity and/or homology, including the comparison of homologs having deletions, additions and/or substitutions relative to a parental sequence, are well known to the practitioner of ordinary skill in the art. On the DNA level, the nucleic acid sequences encoding the homolog of human VEGFR-2 may differ to a larger extent due to the degeneracy of the genetic code.

In yet another preferred embodiment, the eukaryotic expression cassette encodes human VEGFR-2 of the amino acid sequence as found in SEQ ID NO 1.

In certain embodiments, the buffered medium comprises peptone of non-animal origin. In a preferred embodiment, the buffered medium is Tryptic Soy Broth (TSB) of non-animal origin.

In the context of the present invention, "peptone of non-animal origin" refers to refers to a mixture of cleavage products produced by partial acid or enzymatic hydrolysis of native protein which is not of animal origin. Preferably, the native protein is of plant origin. Peptone of non-animal origin solely comprises components that are not directly derived from eukaryotic animals.

In certain embodiments, the volume of the medium is at least about 10 l.

In certain embodiments, the volume of the medium is from at least about 10 l, or 30 l, or 50 l, or 100 l up to a maximum of about 10.000 l, or 1.000 l, or 800 l or 500 l.

In particular embodiments, the volume of the medium is from about 100 l to about 500 l, more particularly about 100 l, about 150 l, about 200 l, about 250 l, about 300 l, about 400 l or about 500 l.

In certain embodiments, the starting glucose concentration corresponds to that of bacterial minimal medium or less.

In certain embodiments, the starting glucose concentration is from about 0 g/l to about 4 g/l.

In particular embodiments, the starting glucose concentration is about 0 g/l, about 0.5 g/l, about 1 WI, about 1.5 WI, about 2 g/l, about 2.5 g/l, about 3 g/l, about 3.5 g/l or about 4 g/l.

In certain embodiments, the starting pH value is from at least about 5, about 6, or about 6.5 up to a maximum of less than about 9, about 8, or about 7.5.

In particular embodiments, the starting pH value is from about 6.5 to about 7.5, more particularly about 7.0.

In a particular embodiment, the pH value is adjusted during culturing to a pH value from about 6 to about 8, particularly to from about 6.5 to about 7.5.

In a particular embodiment, the pH value is adjusted to from at least about 6, or 6.5 up to a maximum of about 8, or about 7.5 during fermentation.

In a particular embodiment, the pH value is adjusted to from about 6.5 to about 7.5 during fermentation, more particularly to about 7.0.

In a particular embodiment, the progress of growth is determined by measuring the optical density (OD).

In the context of the present invention, the term "optical density" or "turbidity" of a material refers to the logarithmic ratio of the radiation falling upon said material to the radiation transmitted through said material for a given wavelength. The optical density is preferably measured using a spectrophotometer. Preferably, the optical density can be used as a measure of the concentration of cells, preferably bacteria, in a suspension. As visible light passes through a cell suspension, the light is scattered. Greater scatter indicates higher cell numbers. Typically, the optical density at a wavelength of 600 nm ($OD_{600}$) is measured. The optical density at a particular wavelength of a bacterial culture plotted against the culturing time gives a growth curve which can be used to delineate the various phases of bacterial growth and to determine the doubling time of bacterial culture. The growth curve is characteristic for a given type of bacteria cultured under given conditions in a given culture medium. Measuring the optical density of a cell suspension can thus be used to monitor the stage of bacterial growth. Optical density measurement can be used to determine the end point of the culturing procedure, i.e. the stage of bacterial growth, in which the cells are to be harvested, typically the mid-log phase of growth.

In a preferred embodiment, the progress of growth is determined by in-situ monitoring of the optical density of the culture or by taking samples and measuring the optical density of the samples. In-situ monitoring of the optical density of a bacterial culture using on-line or in-situ devices allows for constant, continuous, non-invasive monitoring of cell growth, minimizes the risk of contamination and eliminates the need of cumbersome, labor intensive extraction of samples.

It was surprisingly found that growing attenuated mutant strains of Salmonella typhi according to the method of the present invention yields in optical density values of about 6.0 to about 8.0 at the onset of the stationary phase. In comparison, cultivation of the same strain in a similar fermentation process but wherein glucose is added during fermentation to sustain an approximately stable glucose level of about 1 g/l to about 4 g/l yields in optical density values of about 3 to about 5.5. Thus, it was surprisingly found that growing an attenuated mutant strain of Salmonella typhi without addition of glucose to the medium during the fermentation and with a starting glucose amount in the medium that is depleted before reaching the stationary phase yields in an increased optical density at the onset of the stationary phase compared to a fermentation process with glucose addition.

In another embodiment, the progress of growth is determined by measuring the cell density.

In a preferred embodiment, cell density is determined microscopically or by measuring the electrical resistance or by flow cytometry. The cell density can be determined microscopically by manually counting the cells using a counting chamber or hemocytometer. Measuring cell density based on the electrical resistance is preferably performed using a Coulter counter. Measuring the cell density by flow cytometry is achieved by letting the cells pass a laser beam in a narrow stream, which hits them one by one. A light detector picks up the light that is reflected from the cells.

It was surprisingly found that growing attenuated mutant strains of Salmonella typhi according to the method of the present invention yields in cell density values of about $5 \times 10^{14}$ to about $8 \times 10^{14}$ at the onset of the stationary phase. In comparison, cultivation of the same strain in a similar fermentation process but wherein glucose is added during fermentation to sustain an approximately stable glucose level of about 1 g/l to about 4 g/l yields in cell density values of about $5 \times 10^{13}$ to $1 \times 10^{14}$. Thus, it was surprisingly found that growing an attenuated mutant strain of Salmonella typhi without addition of glucose to the medium during the fermentation and with a starting glucose amount in the medium that is depleted before reaching the stationary phase yields in an increased cell density at the onset of the stationary phase compared to a fermentation process with glucose addition.

The optical density of a cell suspension below about 0.4 is directly proportional to its cell density. Thus, a calibration curve can be created by plotting the optical density against the cell density. Such a calibration curve can be used to estimate the cell density of a cell suspension by measuring its optical density.

In another embodiment, the progress of growth is determined by measuring the colony forming units (CFU) value by taking samples and plating on agar plate. By this method, only viable cells are counted as only viable cells are able to form colonies on an agar plate.

It was surprisingly found that growing attenuated mutant strains of Salmonella typhi according to the method of the present invention yields CFU values of about $6 \times 10^9$ to about $8 \times 10^9$ at the onset of the stationary phase. In comparison, cultivation of the same strain in a similar fermentation process but wherein glucose is added during fermentation to sustain an approximately stable glucose level of about 1 g/l to about 4 g/l yields in CFU values of about $2 \times 10^9$ to $5 \times 10^9$. Thus, it was surprisingly found that growing an attenuated mutant strain of Salmonella typhi without addition of glucose to the medium during the fermentation and with a starting glucose amount in the medium that is depleted before reaching the stationary phase not only yields in an increased cell density at the onset of the stationary phase but also in an increased number of viable cells compared to a fermentation process with glucose addition.

In a particular embodiment, the cells are harvested before reaching an optical density of about 6.

In a preferred embodiment, the cells are harvested at an optical density from about 5 to about 6.

In a particular embodiment, the attenuated mutant strain of Salmonella typhi is Salmonella typhi Ty21a and the recombinant DNA molecule comprises the kanamycin resistance gene, the pMB1 ori, and a eukaryotic expression cassette encoding human VEGFR-2, under the control of the CMV promoter.

In a preferred embodiment, human VEGFR-2 has the nucleic acid sequence as found in SEQ ID NO 2.

In yet another aspect, the present invention relates to an attenuated mutant strain of Salmonella typhi lacking galactose epimerase activity and comprising at least one copy of a recombinant DNA molecule comprising an expression cassette, which is obtainable by a method for growing the strain, comprising the step of culturing the strain in a buffered medium comprising peptone at approximately neutral starting pH value at fermentation scale, wherein the amount of glucose in the medium during the fermentations is adjusted such that the amount of glucose is reduced to zero before reaching the stationary phase.

In a particular embodiment, no glucose is added to the medium during the fermentation and the starting amount of glucose is depleted before reaching the stationary phase.

In a particular embodiment, the expression cassette is a eukaryotic expression cassette.

In a particular embodiment, the expression cassette encodes a VEGF receptor protein.

In a preferred embodiment, the eukaryotic expression cassette encodes a VEGF receptor protein selected from the group consisting of human VEGFR-2 and a homolog thereof that shares at least about 80% homology therewith.

In yet another preferred embodiment, the eukaryotic expression cassette encodes human VEGFR-2 of the amino acid sequence as found in SEQ ID NO 1.

In a particular embodiment, the attenuated mutant strain is Salmonella typhi Ty21a and the recombinant DNA molecule comprises the kanamycin resistance gene, the pMB1 ori, and a eukaryotic expression cassette encoding human VEGFR-2 under the control of the CMV promoter.

In a preferred embodiment, human VEGFR-2 has the nucleic acid sequence as found in SEQ ID NO 2.

In another aspect, the present invention relates to an attenuated mutant strain of Salmonella typhi Ty21a comprising at least one copy of a recombinant DNA molecule comprising a eukaryotic expression cassette encoding a VEGF receptor protein for use as a vaccine.

In the context of the present invention, the term "vaccine" refers to an agent which is able to induce an immune response in a subject upon administration. A vaccine can preferably prevent, ameliorate or treat a disease. Preferably, such a vaccine comprises an attenuated mutant strain of Salmonella typhi, preferably S. typhi Ty21a. Preferably, the vaccine further comprises at least one copy of a recombinant DNA molecule comprising an expression cassette, preferably encoding a heterologous antigen. Such a vaccine comprising a vector, for instance an attenuated bacterial strain, as a delivery vehicle for a DNA encoding a heterologous antigen is termed DNA vaccine.

In a particular embodiment, the eukaryotic expression cassette encodes a VEGF receptor protein selected from the group consisting of human VEGFR-2 and a homolog thereof that shares at least about 80% homology therewith.

In a preferred embodiment, the eukaryotic expression cassette encodes human VEGFR-2 of the amino acid sequence as found in SEQ ID NO 1.

In another aspect, the present invention relates to a method for increasing cell growth of an attenuated mutant vaccine strain of *Salmonella*, lacking galactose epimerase activity, by culturing the strain in a buffered medium essentially comprising enzymatic digests of casein and soybean meal and a starting glucose amount of not more than 2.5-3.0 g/L at a starting pH value of 6.5-7.5, wherein culturing is carried out by omitting any additional glucose feeding into the fermentation broth until stationary phase of cell growth, thus not sustaining the original glucose level in the broth, said increase of cell growth, which is solely achieved by fully depletion of glucose during fermentation, is measured by optical density (OD) and has a value of 7.5-8.0 in the finally obtainable stationary phase (preferably obtained after 18-20 h), compared to OD 5.0 to 5.5 in a respective fermentation process under same conditions, wherein however glucose is fed during fermentation to sustain a permanent glucose level in the fermentation broth of 2.0-3.0 g/L.

In a particular embodiment, the maximum cell growth is obtained after 20 h of culturing.

In a particular embodiment, a cell density of $5\times10^{14}$-$8\times10^{14}$ is achieved by omitting any glucose feeding during fermentation, compared to $5\times10^{13}$ to $1\times10^{14}$ when adding glucose during cultivation.

In a particular embodiment, a colony forming unit (CFU) value of $6\times10^9$ to $8\times10^9$ per ml is achieved after fermentation by omitting any glucose feeding during fermentation, compared to $2\times10^9$ to $5\times10^9$ after glucose feeding during fermentation.

In a particular embodiment, the pH value is adjusted during fermentation to 7.0. By omitting glucose feeding in the growth phase or even in the starting medium from the beginning, a shift of the pH values to alkaline (from ca. 7 to ca. 8) can be observed, although the medium system is buffered. It might be favorable to adjust the pH value during cell growth to the original starting pH of ca. 7.0.

In a particular embodiment of the invention, the medium is Tryptic Soy Broth (TSB) or a medium which provides the same or similar nutrients.

In a further preferred embodiment according to the invention the attenuated mutant vaccine strain of *Salmonella* is *Salmonella Typhi* Ty21a.

In another aspect, the invention relates to a method of producing of an attenuated mutant cancer vaccine strain of *Salmonella typhi* Ty21a, wherein the strain carries multiple copies of a plasmid DNA, encoding a eukaryotic expression cassette of human vascular endothelial growth factor receptor 2 (VEGFR-2 or FLK-1), the method comprising a method for increasing cell growth of an attenuated mutant vaccine strain of *Salmonella* of the present invention.

In a particular embodiment said plasmid DNA is a 7580 bp plasmid DNA that comprises the cDNA of VEGFR-2 that is under the control of the CMV promoter, the kanamycin resistance gene, and the pMB1 ori, and that is designated as pVAX10.VR2-1.

SHORT DESCRIPTION OF FIGURES AND TABLES

FIG. 1: Amino acid sequence of VEGFR-2 (SEQ ID NO 1) encoded by cDNA cloned into plasmid pVAX10.VR2-1

FIG. 2: Plasmid map of pVAX10.VR2-1

FIG. 3: Description of manufacturing process of *Salmonella typhi* Ty2a (pVAX10.VR2-1)

FIG. 4: Flow chart of isolation of *S. typhi* Ty21a

FIG. 5: Growth of preculture 1 and 2 of *Salmonella typhi* Ty21a with/without kanamycin FIG. 6: Growth of cultures (preculture 1) of *Salmonella typhi* Ty21a (empty) with glucose pulsing (adjusted to final glucose concentration of 2.5 g/l) and without pulsing of glucose. Cell growth was determined by optical density measurement at 600 nm (OD600). The arrows indicate the addition of glucose (pulsing). X-axis represents culturing time in hours (h); y-axis represents cell density measured in OD units and glucose (glc) concentration in g/l.

FIG. 7: Growth of cultures (preculture 1) of *Salmonella typhi* Ty21a (empty) with glucose pulsing (adjusted to final glucose concentration of 2.5 g/l) and without pulsing of glucose. Cell growth was determined by optical density measurement at 600 nm (OD600). The arrows indicate the addition of glucose (pulsing). X-axis represents culturing time in hours (h); y-axis represents cell density measured in OD units and pH value shift.

FIG. 8: Growth of cultures (preculture 2) of *Salmonella typhi* Ty21a (empty) with glucose pulsing (adjusted to final glucose concentration of 2.5 g/L) and without pulsing of glucose. Cell growth was measured as optical density at 600 nm (00600). The arrows indicate the addition of glucose (pulsing). X-axis represents culturing time in hours (h); y-axis represents cell density measured in OD units and glucose (glc) concentration in g/l.

FIG. 9: Growth of cultures (preculture 2) of *Salmonella typhi* Ty21a (empty) with glucose pulsing (adjusted to final glucose concentration of 2.5 g/l) and without pulsing of glucose. Cell growth was measured as optical density at 600 nm (00600). The arrows indicate the addition of glucose (pulsing). X-axis represents culturing time in hours (h); y-axis represents cell density measured in OD units and pH value shift.

FIG. 10: Growth of cultures (preculture 3, glucose primed inoculums of preculture 1) of *Salmonella typhi* Ty21a (empty) with glucose pulsing (adjusted to final glucose concentration of 2.5 g/l) and without pulsing of glucose. Cell growth was determined by optical density measurement at 600 nm (00600). The arrows indicate the addition of glucose (pulsing). X-axis represents culturing time in hours (h); y-axis represents cell density measured in OD units and glucose (glc) concentration in g/L FIG. 11: Growth of cultures (preculture 3, glucose primed inoculums of preculture 1) of *Salmonella typhi* Ty21a (empty) with glucose pulsing (adjusted to final glucose concentration of 2.5 g/l) and without pulsing of glucose. Cell growth was determined by optical density measurement at 600 nm (00600). The arrows indicate the addition of glucose (pulsing). X-axis represents culturing time in hours (h); y-axis represents cell density measured in OD units and pH value shift.

FIG. 12: Growth of wild-type strain (preculture 1) of *Salmonella typhi* Ty21a compared to engineered cancer vaccine production strain (*Salmonella typhi* Ty21a: pVAX10.VR2-1, VXM01) with glucose pulsing (adjusted to final glucose concentration of 2.5 g/l) and without pulsing of glucose. Cell growth was measured as optical density at 600 nm (OD600). The arrows indicate the addition of glucose (pulsing). X-axis represents culturing time in hours (h); y-axis represents cell density measured in OD units.

FIG. 13: Growth of wild-type strain (preculture 2) of *Salmonella typhi* Ty21a compared to engineered cancer vaccine production strain (*Salmonella typhi* Ty21a:

pVAX10.VR2-1, VXM01) with glucose pulsing (adjusted to final glucose concentration of 2.5 g/l) and without pulsing of glucose. Cell growth was determined by optical density measurement at 600 nm ($OD_{600}$). The arrows indicate the addition of glucose (pulsing). X-axis represents culturing time in hours (h); y-axis represents cell density measured in OD units.

Table 1: Manufacturing process
Table 2: Manufacturing process
Table 3: Results of OD600 measurement during fermentation process
Table 4: Glucose concentration during fermentation process
Table 5: pH-value shift during fermentation process

EXAMPLES

Example 1

Isolation of *Salmonella typhi* Ty21a Strain for the Preparation of the Research Seed Lot (RSL)

The first step in the preparation of the RSL consisted of the isolation of the attenuated *Salmonella typhi* Ty21a strain from TYPHORAL L® (typhoid oral vaccine comprising Ty21a) capsules followed by the transformation of the attenuated bacteria with the plasmid DNA (pVAX10.VR2-1).

The commercially available TYPHORAL L® (typhoid oral vaccine Comprising Ty21a) capsules, containing an attenuated *Salmonella enterica* serovar typhi Ty21a strain, were used to prepare the stock of *S. typhi* to be used in the recombinant studies indicated below The process consisted of inoculating a liquid culture medium with part of the content of the capsules and further plating the liquid culture onto an agar medium for the purpose of isolating single bacterial colonies. Single colonies were isolated and grown in liquid culture medium. Two cultures, namely VAX.Ty21-1 and VAX.Ty21-2, were then formulated with glycerol, aliquoted (1 mL) and stored at −75° C.±5° C. pending use. Identity of each of the two cultures was further confirmed.

Example 2

Plasmid Construction

The principle of plasmid synthesis is based on double strand in vitro gene synthesis with the following steps:

The whole pVAX10-VR2.1 plasmid sequence of 7.58 kB was subdivided (by software analysis) in 5 sections of ~1.5 kB. Each section was subdivided into 40-50 bp oligonucleotides each having overlapping regions between oligonucleotides of both strands The in vitro synthesized oligonucleotides were then phosphorylated by incubation with T4 polynucleotide kinase After the annealing process of overlapping oligonucleotides under appropriate conditions, the Taq DNA ligase enzyme connected the aligned oligonucleotides Upon completion of the ligation step, PCR was performed using primers annealed at outward positions, to increase the yield of the ligated plasmid fragments (~1.5 kB)

A preparative agarose gel electrophoresis was performed to isolate the PCR products The isolated PCR products were cloned into TOPO vectors (Invitrogen K#4575-40) and transformed into TOP10 *E. coli* cells for propagation After TOPO plasmid isolation, a restriction and sequence verification was performed The isolated aligned fragments were assembled via overlap PCR. This process was followed by linearly assembling the pVAX10.VR2-1 plasmid After XhoI restriction digest (single restriction site is present in the pVAX10.VR2-1 plasmid, see FIG. 2.1.S.1.2.2-1) and covalent binding via T4 ligase, *E. coli* was transformed with the circular plasmid for propagation After final plasmid sequence verification, the pVAX10.VR2-1 plasmid was transformed into the *S. typhi* Ty21a bacterial strain.

The plasmid pVAX10.VR2-1 was thus successfully synthesized (no deviation to reference sequence). This plasmid was further used to transform the *S. typhi* Ty21a bacterial strain isolates (Vax.Ty21-1 and Vax.Ty21-2).

Example 3

Manufacturing Processes

The following Table 2 summarizes the processes of manufacture with/without glucose feeding during fermentation.

| Production step | Process variant A: with glucose feeding | Process variant A: without glucose feeding |
|---|---|---|
| Preculture Clean room class D and A in D | CELLS (with/without plasmid pVAX10.VR2-1) ↓ 350 mL TSP + kanamycin (1 mL) ↓ 5 × 550 mL TSB + kanamycin (50 mL) | CELLS (with or without plasmid pVAX10.VR2-1) ↓ 2 × 500 ml TSB + kanamycin (500 μL) ($OD_{600}$ > 0.3) ↓ 10 × 1000 ml TSB + kanamycin (75 mL) ($OD_{600}$ ≥ 0.5) |

| Production step | Process variant A: with glucose feeding | Process variant A: without glucose feeding |
|---|---|---|
| Fermentation<br>Clean room<br>class D | 30 L Fermentation volume<br>TSB + 0.001% galactose<br>30° C.<br>Airflow 2 l/min (0.07 vvm)<br>pressure 1 bar<br>pH 7.0 controlled with NaOH<br>pO2 ≥ 40 % regulated by stirrer<br>glucose feeding Σ 5-8 g/l<br>Final $OD_{600\,nm}$~2.7 (target 6-10)<br>Cooling to 15° C. before harvest | 100 L Fermentation volume<br>TSB + 0.001% galactose<br>30° C.<br>Airflow 100 L/min (1 vvm)<br>pressure not controlled<br>pH 7.0 controlled with NaOH<br>foam controlled (Corning)<br>pO2 ≥ 40 % regulated by stirrer<br>stirrer minimum 200 rpm<br>no glucose feeding<br>Final $OD_{600\,nm}$ (end of exponential growth phase)<br>Cooling to at least 25° C. before harvest |
| Harvest/<br>concentration/<br>wash<br>Clean room<br>class D | Cross flow filtration<br>10 fold concentration<br>10 fold buffer exchange on diafiltration<br>with 15% sucrose solution, followed by<br>further concentration to 1/15 vol of<br>original harvest<br>Formulation by adding ascorbate to final<br>concentration of 0.45%<br>Storage at 2-8° C. until filling 24 hours | Cross flow filtration<br>10 fold concentration<br>10 fold buffer exchange on diafiltration with 15%<br>sucrose, 0.35% ascorbate solution pH 7.2, followed<br>by further concentration 10 1/20 vol. of original harvest<br>Storage* at 2-8° C. until filling about 24 hours |
| Dilution/filling<br>of vials<br>Clean room<br>class A in B | Manual filling of 150 vials of 5 dilutions<br>Adjustment of CFU<br>300 mL suspension → filling of 150 vials<br>Dilution of 30 mL suspension 270 mL<br>formulation solution, filling of 150 2<br>R glass vials<br>Four dilutions and filling of 150 vials until<br>1:10.000<br>Closing of vials with rubber stoppers and<br>aluminium caps<br>Storage at −75° C. ± 10° C. | Manual filling of 150 vials of 5 dilutions<br>Adjustment of CFU<br>300 mL suspension → filling of 150 vials<br>Dilution of 30 mL suspension 270 mL formulation<br>solution, filling 150 2 R glass vials<br>Four dilutions and filling of 150 vials until 1:10.000<br>Closing of vials with rubber stoppers and aluminium<br>caps<br>Storage at ≤ −70° C. |

The bacterial growth process was carried out in 2×350 ml TSB medium further containing 25 μg/ml kanamycin. Two 2-L-Erlenmeyer flasks with baffles were inoculated each with an aliquot (1 ml) of *Salmonella typhi* Ty21a and Ty21a (pVAX10.VR2-1). The cultures were incubated at 30° C.±2° C. with shaking (140 rpm) until an Optical Density $OD_{600nm}$>0.1 was reached. The bacterial harvest (50 ml) of the first culture was used to inoculate a second culture (pre-culture 2), 6×550 ml TSB medium with kanamycin (25 μg/ml) contained in 3-l-Fernbach flasks with baffles. The cultures were incubated at 30° C.±2° C. with shaking (180 rpm) until an OD at 600 nm of the bacterial culture reached a value of ≥0.3. Upon completion of the incubation time, the main culture (TSB medium with 0.001% galactose) prepared in a controlled stainless-steel fermenter with a working volume of 27 l, was inoculated with the pre-culture 2 (pooled 5 flasks of bacterial culture) and incubated at 30° C. with the following settings: airflow at 2 l/min, pressure at 1 bar, pH 7.0, $pO_2$≥40%.

One half of the culture samples was fed with glucose in an amount that gave a final concentration of 2.0 g/l to 3.0 g/l in the starting culture medium. Glucose feeding was carried out after 3-5 h after onset of fermentation and was repeated several times each 3-5 h.

The other half of the culture samples was treated identically but without any feeding of glucose during cultivation of *Salmonella* cells. As a control, a culture medium was tested that did not contain any glucose from the very first beginning (TSB medium without glucose).

The bacterial culture was concentrated by cross-flow filtration (CFF)/diafiltration against a 15% sucrose solution. Five dilutions of the final bacterial concentrate were carried out. The final bacterial product was then aliquoted (1 ml) in 2R vials, the vials closed, labeled, capped and stored at −75° C.±5° C.

In-process controls for the first and second pre-culture steps, at the completion of the incubation times, included analysis of bacterial growth by measuring $OD_{600nm}$, pH and CFU/mL as well as determination of plasmid stability (PST) and bacterial examination. The latter analysis was based on a blood agar assay for determining hemolytic reactions of fastidious pathogenic microorganisms. The CFU value was assessed before and after the CFF. Upon formulation of the final bacterial concentrate, CFU and refractive index were measured on the formulation with the lowest bacterial concentration.

Example 4

Growth of *Salmonella typhi* TY21a (pVAX10.VR2-1) with and without Kanamycin The production of the live bacterial cancer vaccine is based on the fermentation of a *Salmonella enterica* serovar typhi strain Ty21a (comprising the plasmid pVAX10.VR2-1). After growth the cell suspension has to be concentrated by crossflow filtration and washed by diafiltration. Five different dilutions of washed cell suspension have to be filled in 2 R glass vials.

The aims of these flask growth tests were:

verifying growth rate for preculture 1 and 2 for planning time table of production run investigating the influence of glucose feeding to achieve high cell concentration (OD600 values)

Experiments were performed starting from the master cell banks of *Salmonella enterica* typhi TY21a and *Salmonella enterica* typhi TY21a (pVAX10.VR2-1) (=strain VMX01). Inoculum for fermentation was prepared by a two-step preculture (VK): Preculture 1 was inoculated directly from MCB; preculture 2 was inoculated by a larger volume out of preculture 1. Growth tests were performed to evaluate time course for cultivating preculture in 2 l Erlenmeyer flasks (preculture 1) and 3 l Fernbach Corning flasks (preculture 2) growth tests. Preculture was done with and without kanamycin to get information about growth/exponential growth phase at both conditions.

Figure 5:
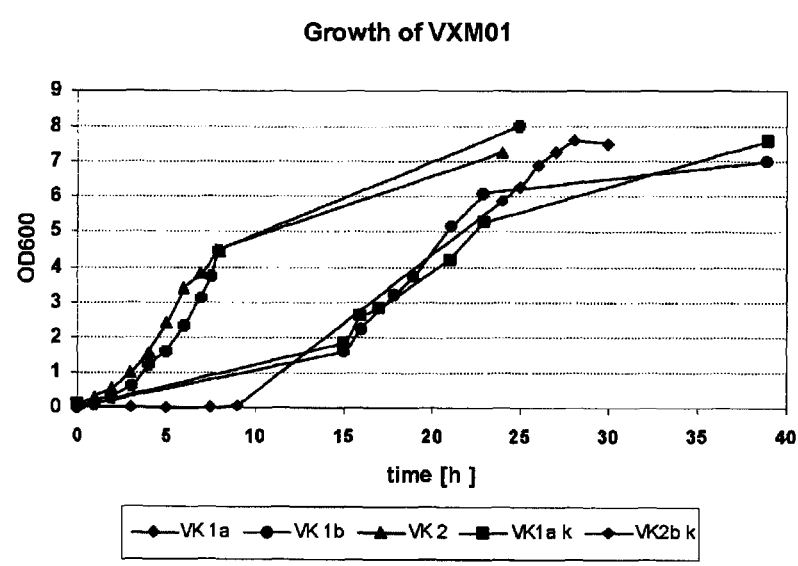
Figure 6:
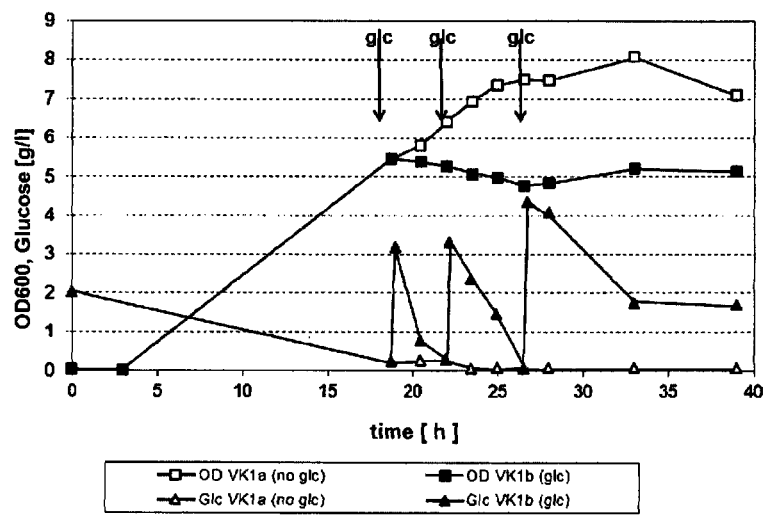
Figure 7:
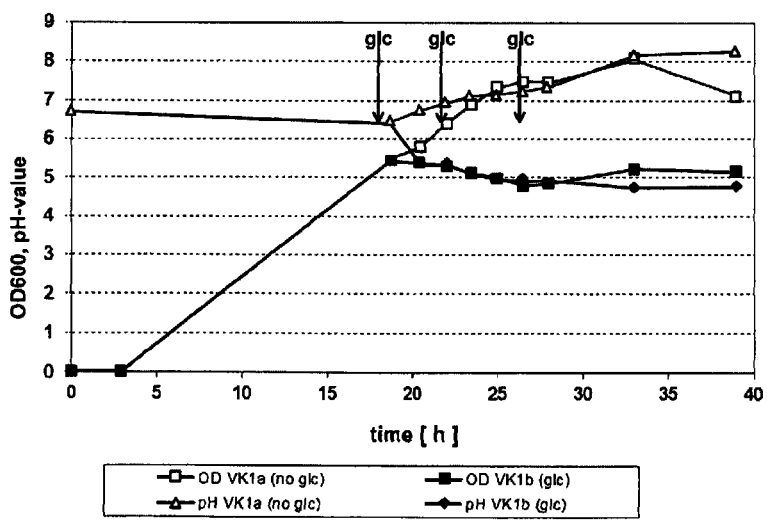

Growth of these five flasks is compared in FIG. 5:
VK1a: 500 ml TSB Medium in 3 l Corning flask+0.5 ml MCB, 30° C., 120 rpm
VK1b: 500 ml TSB Medium in 3 l Corning flask+0.5 ml MCB, 30° C., 120 rpm
VK2: 1000 ml TSB Medium in 3 l Corning flask+75 ml VK1b (OD 1, 6), 30° C., 120 rpm
VK1a k: 500 ml TSB Medium+25 mg/l kanamycin sulfate in 2 l Corning flask+0.5 ml MCB, 30° C., 120 rpm
VK1b k: 500 ml TSB Medium+25 mg/l kanamycin sulfate in 3 l Corning flask+0.5 ml MCB, 30° C., 120 rpm
VK2a k: 1000 ml TSB Medium+25 mg/l kanamycin sulfate in 3 l Corning flask+75 ml VK1a k (OD 1, 8), 30° C., 120 rpm
VK2b k: 1000 ml TSB Medium+25 mg/l kanamycin sulfate in 3 l Corning flask+75 ml VK1a k (OD 1, 8), 30° C., 120 rpm The results in FIG. 5 show, that there are no significant differences between growth with and without kanamycin as well as in growth in 2 l or 3 l Corning flask respectively. Cultivation time for preculture 1 at 30° C. should be between about 15 to 23 hours ($OD_{600}$~1-4) to inoculate preculture 2 with cells in exponential phase. Minimum $OD_{600}$ for preculture 2 (>0.5) was achieved after 2-3 hours; exponential growth phase is characterized by OD600 values between 0.5 and 3.0.

Example 5

Growth of *Salmonella typhi* TY21a (Empty) with and without Glucose Feeding

Growth tests with three precultures (1, 2, 3) were performed in 2 l Erlenmeyer flasks and two step culture as done with the production strain.

Preculture 1 is inoculated directly from RCB; preculture 2 is inoculated by a larger volume out of preculture 1. Due to absence of plasmid encoded kanamycin resistance, selective antibiotic was omitted in culture media. To evaluate the influence of preculture step (generation number), repeated glucose additions were done in preculture 1 as well as in preculture 2, both in comparison to "unpulsed" cultures. In addition, glucose pulsed preculture 1 was used as inoculum for preculture 2 to follow up the reversibility of glucose concentration mediated metabolic impact. Preculture 3 represents preculture 1 grown with glucose feeding (pulsing) inoculated into fresh TSB medium (with or without glucose).

The sample designations as used in FIGS. 6-11 are as follows:
VK1a: 500 ml TSB Medium in 2 l Corning flask+0.5 ml RCB, 30° C., 120 rpm
VK1b: 500 ml TSB Medium in 2 l Corning flask+0.5 ml RCB, 30° C., 120 rpm+glucose addition
VK2a: 500 ml TSB Medium in 2 l Corning flask+38 ml VK1a (OD 5, 4), 30° C., 120 rpm VK2b: 500 ml TSB Medium in 2 l Corning flask+38 ml VK1a (OD 5, 4), 30° C., 120 rpm+glucose addition
VK3a: 500 ml TSB Medium in 2 L Corning flask+38 ml VK1b (OD 5, 1; 5 hours after first glucose addition) 30° C., 120 rpm
VK3b: 500 ml TSB Medium in 2 L Corning flask+38 ml VK1b (OD 5, 1; 5 hours after first glucose addition) 30° C., 120 rpm+glucose addition.

The results of these experiments show that glucose addition does not result in higher OD-values/cell mass yields of the wild type strain despite of glucose consumption. In contrast, flasks without glucose addition reached higher OD values (6 for preculture 1, 8 for preculture 2). Approx. 1 h after glucose addition OD remained static (or even slightly declined) compared to growth without glucose addition. On repeated pulses glucose consumption declined, no additional/additive effect on growth was observed.

Without glucose addition a shift of pH to alkaline was observed after depletion of glucose while with glucose pulse pH-value dropped (compare FIG. 8 for preculture 1 and FIG. 9 for preculture 2). Phenomena were observed in both precultures (VK1, VK2), indicating no influence of generation number.

Figure 10:
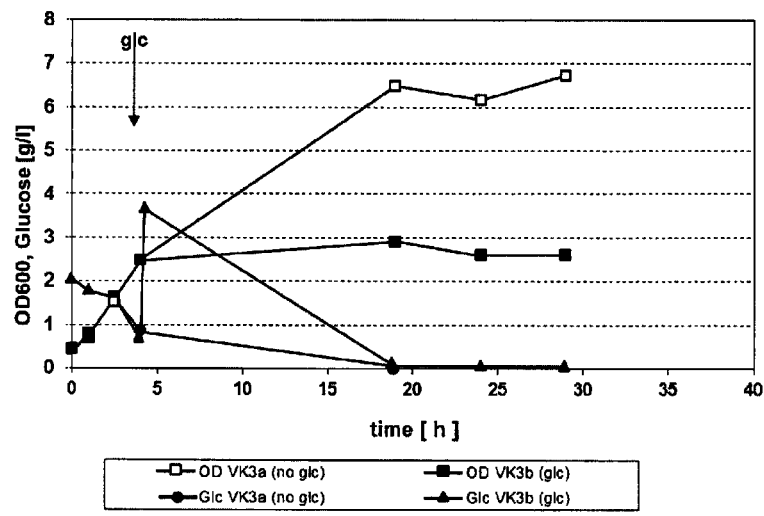
Figure 11:
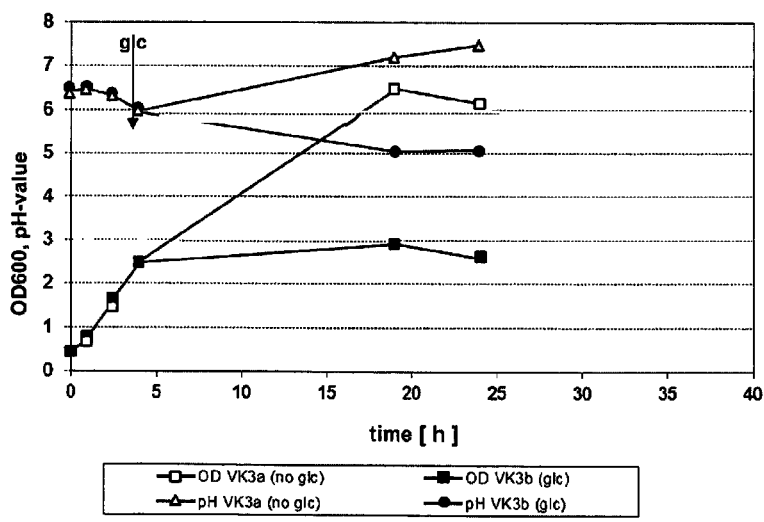

When a preculture grown with glucose pulse was inoculated into fresh medium (1:14 dilution; VK3; FIG. 10, FIG. 11), the same growth characteristics (higher OD values/pH shift to alkaline without glucose addition) were observed.

Results indicated that glucose concentrations above a comparably low limit (approx. 2.5 g/l) trigger a reversible change in (glucose) metabolism. Presumably, a substance is then secreted into medium which inhibits further growth, even if glucose declines again below trigger level. After inoculation in new medium (VK3) this substance is diluted to a concentration beneath effectiveness.

Example 6

Growth of Engineered Production Cancer Vaccine Strain *Salmonella typhi* Ty21a (pVAX10.VR2-1) (=VXM01) with and without Glucose Feeding The same experimental approach as described in Example 5 was carried out with the cancer vaccine production strain VXM01. The only difference to Example 5 is that the strain was transformed with plasmid pVAX10.VR2-1. These investigations were made to support the hypothesis, that the growth characteristics of the production strain *S. typhi* Ty21a:pVAX10-VR2.1 (p) regarding the glucose metabolism is not influenced by the plasmid but a characteristic of the empty strain. Growth and glucose pulse of both strains are compared in FIG. 11 and FIG. 12.

The results show, that growth characteristics of both strains (*S. typhi* Ty21a empty and engineered production strain) are comparable. No indication for influence of the plasmid was seen. Moreover, although the cells grown without glucose show a different morphology compared to the cells grown in the presence of glucose, they show no increased cell lysis and no decreases plasmid stability (in case of the engineered cells) as compared to the cells grown with glucose.

TABLE 3

Results of OD600 measurement during fermentation process

| Cultivation time [h] | VK1a | VK1b | VK2 | VK1a k | VK1b k | VK2a k | VK2b k |
|---|---|---|---|---|---|---|---|
| 0 | 0.001 | 0.003 | 0.1 | 0.0 | 0.0 | 0.2 | 0.2 |
| 1 | | | 0.3 | | | 0.3 | 0.3 |
| 2.0 | | | 0.5 | | | 0.7 | 0.6 |
| 3.0 | 0.003 | | 1.0 | | | 1.2 | 1.2 |
| 4.0 | | | 1.6 | | | 1.7 | 1.6 |
| 5.0 | 0.005 | | 2.4 | | | 2.5 | 2.3 |
| 6.0 | | | 3.4 | | | 3.1 | 3.1 |
| 7.0 | | | 3.8 | | | 3.7 | 3.7 |
| 7.5 | 0.010 | | | | | 3.7 | 4.5 |
| 8.0 | | | 4.5 | | | | |
| 9.0 | 0.026 | | | | | | |
| 10.0 | | | | | | | |
| 11.0 | | | | | | | |
| 12.0 | | | | | | | |
| 13.0 | | | | | | | |
| 14.0 | | | | | | | |
| 15.0 | | 1.6 | | 1.8 | 2.1 | | |
| 16.0 | | 2.2 | | 2.6 | 2.8 | | |
| 17.0 | | 2.8 | | 2.8 | 3 | | |
| 18.0 | | 3.2 | | | 3.1 | | |
| 19.0 | | 3.7 | | | 3.0 | | |
| 20.0 | | | | | | | |
| 21.0 | | 5.1 | | 4.2 | 3 | | |
| 22.0 | | | | | | | |
| 23.0 | | 6.1 | | 5.3 | 3.1 | | |
| 24.0 | 5.9 | | 7.3 | | | 3.8 | 8 |
| 25.0 | 6.3 | | | | | | |
| 26.0 | 6.9 | | | | | | |
| 27.0 | 7.3 | | | | | | |
| 28.0 | 7.6 | | | | | | |
| 30.0 | 7.5 | | | | | | |
| 39.0 | | 7.0 | | 7.6 | 3.2 | | |

TABLE 4

Glucose concentration during fermentation process

| Cultivation time [h] | VK1a k | VK1b k | VK2a k | VK2b k |
|---|---|---|---|---|
| 0 | 2.4 | 2.4 | 2.5 | 2.6 |
| 1 | | | 2.5 | |
| 2.0 | | | 2.4 | |
| 3.0 | | | 2.3 | |
| 4.0 | | | 1.7 | |
| 5.0 | | | 4.8 | 1.0 |
| 6.0 | | | 3.9 | 0.1 |
| 7.0 | | | 3.1 | |
| 7.5 | | | | |
| 8.0 | | | 2.2 | |
| 9.0 | | | | |
| 10.0 | | | | |
| 11.0 | | | | |
| 12.0 | | | | |
| 13.0 | | | | |
| 14.0 | | | | |
| 15.0 | 1.4 | 1.1 | | |
| 16.0 | 0.4 | 0.1 | | |
| 17.0 | | 3.8 | | |
| 18.0 | | 3.2 | | |
| 19.0 | | 2.5 | | |
| 20.0 | | | | |
| 21.0 | | 1.6 | | |
| 22.0 | | | | |
| 23.0 | | 0.8 | | |
| 24.0 | | | 0 | |
| 25.0 | | | | |
| 26.0 | | | | |
| 27.0 | | | | |
| 28.0 | | | | |
| 30.0 | | | | |
| 39.0 | | 0.0 | | |

TABLE 5 pH-value shift during fermentation process

| Incubation time [h] | VK1a k pH | VK1b k pH | VK2a k pH | VK2b k pH |
|---|---|---|---|---|
| 0 | 6.8 | 6.8 | 6.5 | 6.5 |
| 1 | | | 6.4 | 6.4 |
| 2.0 | | | 6.4 | 6.4 |
| 3.0 | | | 6.5 | 6.5 |
| 4.0 | | | 6.0 | 6.0 |
| 5.0 | | | 6.2 | 6.2 |
| 6.0 | | | 5.8 | 5.91 |
| 7.0 | | | | |
| 7.5 | | | | |
| 8.0 | | | 5.4 | 5.9 |
| 9.0 | | | | |
| 10.0 | | | | |
| 11.0 | | | | |
| 12.0 | | | | |
| 13.0 | | | | |
| 14.0 | | | | |
| 15.0 | 5.7 | 5.6 | | |
| 16.0 | 5.6 | 5.6 | | |
| 17.0 | 5.7 | 5.4 | | |
| 18.0 | 5.8 | 4.4 | | |
| 19.0 | 5.7 | 5.3 | | |
| 20.0 | | | | |
| 21.0 | 6.1 | 5.2 | | |
| 22.0 | | | | |
| 23.0 | 6.6 | 5.1 | | |
| 24.0 | | | 5.7 | 8.28 |
| 25.0 | | | | |
| 26.0 | | | | |
| 27.0 | | | | |
| 28.0 | | | | |
| 30.0 | | | | |
| 39.0 | 8.0 | 5.1 | | |

The invention claimed is:

1. A method for growing an attenuated mutant strain of *Salmonella typhi* lacking galactose epimerase activity and comprising at least one copy of a recombinant DNA molecule comprising a eukaryotic expression cassette, comprising the step of culturing the strain in a buffered medium comprising peptone at approximately neutral starting pH value at fermentation scale, wherein no glucose is added to the medium during the fermentation, wherein the amount of glucose in the medium during the fermentation is adjusted such that the amount of glucose is reduced to zero before reaching the stationary phase, and wherein the volume of the medium is at least about 10 l.

2. The method of claim 1, wherein said attenuated mutant strain of *Salmonella typhi* is *Salmonella typhi* Ty21a.

3. The method of claim 1, wherein the expression cassette encodes a vascular endothelial growth factor (VEGF) receptor protein selected from the group consisting of human vascular endothelial growth factor receptor-2 (VEGFR-2) having the amino acid sequence as found in SEQ ID NO 1 and a homolog thereof that shares at least about 80% homology therewith.

4. The method of claim 1, wherein the buffered medium comprises peptone of non-animal origin.

5. The method of claim 1, wherein the volume of the medium is from about 10 l to about 10,000 l, or from about 30 l to about 1,000 l, or from about 100 l to about 500 l.

6. The method of claim 1, wherein the starting glucose concentration is from about 0 g/l to about 4 g/l.

7. The method of claim 1, wherein the starting pH value is from about 6 to about 8, or from about 6.5 to about 7.5.

8. The method of claim 1, wherein the pH value is adjusted during said culturing to a pH value of about 6 to about 8, or to a pH value of about 6.5 to about 7.5.

9. The method of claim 1, wherein the progress of growth is determined by (i) measuring the optical density (OD), or by (ii) measuring the cell density, or by (iii) measuring the colony forming units (CFU) value by taking samples and plating on agar plates.

10. The method of claim 1, wherein the cells are harvested before reaching an optical density of about 6, when measured at a wavelength of 600 nm.

11. The method of claim 1, wherein the attenuated mutant strain of *Salmonella typhi* is *Salmonella typhi* Ty21a and the recombinant DNA molecule comprises a kanamycin resistance gene, a pMB1 origin of replication (ori), and a eukaryotic expression cassette encoding human VEGFR-2, under the control of the cytomegalovirus (CMV) promoter.

12. The method of claim 4, wherein the buffered medium is Tryptic Soy Broth (TSB) of non-animal origin.

13. The method of claim 1 or claim 9, wherein the progress of growth is determined by (i) measuring the optical density (OD) by (ia) in-situ monitoring of the optical density of the culture or by (ib) taking samples and measuring the optical density of the samples, or by (ii) measuring the cell density (iia) microscopically or (iib) by measuring the electrical resistance, or (iic) by flow cytometry, or by (iii) measuring the colony forming units (CFU) value by taking samples and plating on agar plates.

14. The method of claim 1, wherein the cells are harvested at an optical density of about 6, when measured at a wavelength of 600 nm.

15. The method of claim 11, wherein human VEGFR-2 has the nucleic acid sequence as found in SEQ ID NO 2.

* * * * *

SEQUENCE LISTING

<160> NUMBER OF SEQ ID NOS: 2

<210> SEQ ID NO 1
<211> LENGTH: 1356
<212> TYPE: PRT
<213> ORGANISM: Homo sapiens

<400> SEQUENCE: 1

```
Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415
```

```
Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
            435                 440                 445

Ala Ile Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
            515                 520                 525

Lys Cys Glu Ala Val Asn Lys Val Gly Arg Gly Glu Arg Val Ile Ser
            530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
            595                 600                 605

Leu Trp Lys Leu Asn Ala Thr Met Phe Ser Asn Ser Thr Asn Asp Ile
610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
            675                 680                 685

Thr Ala Ser Gly Asn Pro Pro Pro Gln Ile Met Trp Phe Lys Asp Asn
            690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Leu
            755                 760                 765

Val Gly Thr Ala Val Ile Ala Met Phe Phe Trp Leu Leu Val Ile
            770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
            805                 810                 815

Cys Glu Arg Leu Pro Tyr Asp Ala Ser Lys Trp Glu Phe Pro Arg Asp
            820                 825                 830
```

-continued

```
Arg Leu Lys Leu Gly Lys Pro Leu Gly Arg Gly Ala Phe Gly Gln Val
            835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
            885                 890                 895

Asn Val Val Asn Leu Leu Gly Ala Cys Thr Lys Pro Gly Gly Pro Leu
            900                 905                 910

Met Val Ile Val Glu Phe Cys Lys Phe Gly Asn Leu Ser Thr Tyr Leu
            915                 920                 925

Arg Ser Lys Arg Asn Glu Phe Val Pro Tyr Lys Thr Lys Gly Ala Arg
            930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
            965                 970                 975

Phe Val Glu Glu Lys Ser Leu Ser Asp Val Glu Glu Glu Ala Pro
            980                 985                 990

Glu Asp Leu Tyr Lys Asp Phe Leu  Thr Leu Glu His Leu  Ile Cys Tyr
            995                 1000                1005

Ser Phe  Gln Val Ala Lys Gly  Met Glu Phe Leu Ala  Ser Arg Lys
    1010                1015                1020

Cys Ile  His Arg Asp Leu Ala  Ala Arg Asn Ile Leu  Leu Ser Glu
    1025                1030                1035

Lys Asn  Val Val Lys Ile Cys  Asp Phe Gly Leu Ala  Arg Asp Ile
    1040                1045                1050

Tyr Lys  Asp Pro Asp Tyr Val  Arg Lys Gly Asp Ala  Arg Leu Pro
    1055                1060                1065

Leu Lys  Trp Met Ala Pro Glu  Thr Ile Phe Asp Arg  Val Tyr Thr
    1070                1075                1080

Ile Gln  Ser Asp Val Trp Ser  Phe Gly Val Leu Leu  Trp Glu Ile
    1085                1090                1095

Phe Ser  Leu Gly Ala Ser Pro  Tyr Pro Gly Val Lys  Ile Asp Glu
    1100                1105                1110

Glu Phe  Cys Arg Arg Leu Lys  Glu Gly Thr Arg Met  Arg Ala Pro
    1115                1120                1125

Asp Tyr  Thr Thr Pro Glu Met  Tyr Gln Thr Met Leu  Asp Cys Trp
    1130                1135                1140

His Gly  Glu Pro Ser Gln Arg  Pro Thr Phe Ser Glu  Leu Val Glu
    1145                1150                1155

His Leu  Gly Asn Leu Leu Gln  Ala Asn Ala Gln Gln  Asp Gly Lys
    1160                1165                1170

Asp Tyr  Ile Val Leu Pro Ile  Ser Glu Thr Leu Ser  Met Glu Glu
    1175                1180                1185

Asp Ser  Gly Leu Ser Leu Pro  Thr Ser Pro Val Ser  Cys Met Glu
    1190                1195                1200

Glu Glu  Glu Val Cys Asp Pro  Lys Phe His Tyr Asp  Asn Thr Ala
    1205                1210                1215

Gly Ile  Ser Gln Tyr Leu Gln  Asn Ser Lys Arg Lys  Ser Arg Pro
    1220                1225                1230

Val Ser  Val Lys Thr Phe Glu  Asp Ile Pro Leu Glu  Glu Pro Glu
```

| | | | | | | | | | | |
|---|---|---|---|---|---|---|---|---|---|---|
| | | 1235 | | | 1240 | | | 1245 | | |
| Val | Lys | Val | Ile | Pro | Asp | Asp | Asn | Gln | Thr | Asp | Ser | Gly | Met | Val |
| | 1250 | | | | 1255 | | | | 1260 | |
| Leu | Ala | Ser | Glu | Glu | Leu | Lys | Thr | Leu | Glu | Asp | Arg | Thr | Lys | Leu |
| | 1265 | | | | 1270 | | | | 1275 | |
| Ser | Pro | Ser | Phe | Gly | Gly | Met | Val | Pro | Ser | Lys | Ser | Arg | Glu | Ser |
| | 1280 | | | | 1285 | | | | 1290 | |
| Val | Ala | Ser | Glu | Gly | Ser | Asn | Gln | Thr | Ser | Gly | Tyr | Gln | Ser | Gly |
| | 1295 | | | | 1300 | | | | 1305 | |
| Tyr | His | Ser | Asp | Asp | Thr | Asp | Thr | Thr | Val | Tyr | Ser | Ser | Glu | Glu |
| | 1310 | | | | 1315 | | | | 1320 | |
| Ala | Glu | Leu | Leu | Lys | Leu | Ile | Glu | Ile | Gly | Val | Gln | Thr | Gly | Ser |
| | 1325 | | | | 1330 | | | | 1335 | |
| Thr | Ala | Gln | Ile | Leu | Gln | Pro | Asp | Ser | Gly | Thr | Thr | Leu | Ser | Ser |
| | 1340 | | | | 1345 | | | | 1350 | |
| Pro | Pro | Val |
| | 1355 | |

<210> SEQ ID NO 2
<211> LENGTH: 4071
<212> TYPE: DNA
<213> ORGANISM: Homo sapiens

<400> SEQUENCE: 2

```
atgcagagca aggtgctgct ggccgtcgcc ctgtggctct gcgtggagac ccgggccgcc      60
tctgtgggtt tgcctagtgt ttctcttgat ctgcccaggc tcagcataca aaaagacata     120
cttacaatta aggctaatac aactcttcaa attacttgca ggggacagag ggacttggac     180
tggctttggc ccaataatca gagtggcagt gagcaagggg tggaggtgac tgagtgcagc     240
gatggcctct tctgtaagac actcacaatt ccaaaagtga tcggaaatga cactggagcc     300
tacaagtgct ctaccgggaa actgacttgg cctcggtca tttatgtcta tgttcaagat     360
tacagatctc catttattgc ttctgttagt gaccaacatg gagtcgtgta cattactgag     420
aacaaaaaca aaactgtggt gattccatgt ctcgggtcca tttcaaatct caacgtgtca     480
cttgtgcaa gatacccaga aaagagattt gttcctgatg gtaacagaat ttcctgggac     540
agcaagaagg gctttactat tcccagctac atgatcagct atgctggcat ggtcttctgt     600
gaagcaaaaa ttaatgatga agttaccag tctattatgt acatagttgt cgttgtaggg     660
tataggattt atgatgtggt tctgagtccg tctcatggaa ttgaactatc tgttggagaa     720
aagcttgtct taaattgtac agcaagaact gaactaaatg tggggattga cttcaactgg     780
gaataccctt cttcgaagca tcagcataag aaacttgtaa accgagacct aaaaacccag     840
tctgggagtg agatgaagaa atttttgagc accttaacta tagatggtgt aacccggagt     900
gaccaaggat gtacacctg tgcagcatcc agtgggctga tgaccaagaa gaacagcaca     960
tttgtcaggg tccatgaaaa acctttttgtt gcttttggaa gtggcatgga atctctggtg    1020
gaagccacgg tggggagcg tgtcagaatc cctgcgaagt accttggtta cccaccccca    1080
gaaataaaat ggtataaaaa tggaataccc cttgagtcca atcacacaat taaagcgggg    1140
catgtactga cgattatgga agtgagtgaa agagacacag gaattacac tgtcatcctt    1200
accaatccca tttcaaagga gaagcagagc catgtggtct ctctggttgt gtatgtccca    1260
ccccagattg tgagaaatc tctaatctct cctgtggatt cctaccagta cggcaccact    1320
caaacgctga catgtacggt ctatgccatt cctccccgc atcacatcca ctggtattgg    1380
```

```
cagttggagg aagagtgcgc caacgagccc agccaagctg tctcagtgac aaacccatac    1440
ccttgtgaag aatggagaag tgtggaggac ttccagggag gaaataaaat tgaagttaat    1500
aaaaatcaat ttgctctaat tgaaggaaaa aacaaaactg taagtaccct tgttatccaa    1560
gcggcaaatg tgtcagcttt gtacaaatgt gaagcggtca acaaagtcgg gagaggagag    1620
agggtgatct ccttccacgt gaccaggggt cctgaaatta ctttgcaacc tgacatgcag    1680
cccactgagc aggagagcgt gtctttgtgg tgcactgcag acagatctac gtttgagaac    1740
ctcacatggt acaagcttgg cccacagcct ctgccaatcc atgtgggaga gttgcccaca    1800
cctgtttgca agaacttgga tactcttttgg aaattgaatg ccaccatgtt ctctaatagc    1860
acaaatgaca ttttgatcat ggagcttaag aatgcatcct tgcaggacca aggagactat    1920
gtctgccttg ctcaagacag gaagaccaag aaaagacatt gcgtggtcag gcagctcaca    1980
gtcctagagc gtgtggcacc cacgatcaca ggaaacctgg agaatcagac gacaagtatt    2040
ggggaaagca tcgaagtctc atgcacggca tctgggaatc cccctccaca gatcatgtgg    2100
tttaaagata atgagaccct tgtagaagac tcaggcattg tattgaagga tgggaaccgg    2160
aacctcacta tccgcagagt gaggaaggag gacgaaggcc tctacacctg ccaggcatgc    2220
agtgttcttg gctgtgcaaa agtggaggca ttttttcataa tagaaggtgc ccaggaaaag    2280
acgaacttgg aaatcattat tctagtaggc acggcggtga ttgccatgtt cttctggcta    2340
cttcttgtca tcatcctacg gaccgttaag cgggccaatg gaggggaact gaagacaggc    2400
tacttgtcca tcgtcatgga tccagatgaa ctcccattgg atgaacattg tgaacgactg    2460
ccttatgatg ccagcaaatg ggaattcccc agagaccggc tgaagctagg taagcctctt    2520
ggccgtggtg cctttggcca agtgattgaa gcagatgcct ttggaattga caagacagca    2580
acttgcagga cagtagcagt caaaatgttg aaagaaggag caacacacag tgagcatcga    2640
gctctcatgt ctgaactcaa gatcctcatt catattggtc accatctcaa tgtggtcaac    2700
cttctaggtg cctgtaccaa gccaggaggg ccactcatgg tgattgtgga attctgcaaa    2760
tttggaaacc tgtccactta cctgaggagc aagagaaatg aatttgtccc ctacaagacc    2820
aaaggggcac gattccgtca agggaaagac tacgttggag caatccctgt ggatctgaaa    2880
cggcgcttgg acagcatcac cagtagccag agctcagcca gctctggatt tgtggaggag    2940
aagtccctca gtgatgtaga agaagaggaa gctcctgaag atctgtataa ggacttcctg    3000
accttggagc atctcatctg ttacagcttc caagtggcta agggcatgga gttcttggca    3060
tcgcgaaagt gtatccacag ggacctggcg gcacgaaata tcctcttatc ggagaagaac    3120
gtggttaaaa tctgtgactt tggcttggcc cgggatattt ataaagatcc agattatgtc    3180
agaaaaggag atgctcgcct ccctttgaaa tggatggccc cagaaacaat ttttgacaga    3240
gtgtacacaa tccagagtga cgtctggtct tttggtgttt tgctgtggga aatattttcc    3300
ttaggtgctt ctccatatcc tggggtaaag attgatgaag aattttgtag gcgattgaaa    3360
gaaggaacta gaatgagggc ccctgattat actacaccag aaatgtacca gaccatgctg    3420
gactgctggc acggggagcc cagtcagaga cccacgtttt cagagttggt ggaacatttg    3480
ggaaatctct tgcaagctaa tgctcagcag gatggcaaag actacattgt tcttccgata    3540
tcagagactt tgagcatgga agaggattct ggactctctc tgcctacctc acctgtttcc    3600
tgtatggagg aggaggaagt atgtgacccc aaattccatt atgacaacac agcaggaatc    3660
agtcagtatc tgcagaacag taagcgaaag agccggcctg tgagtgtaaa aacatttgaa    3720
```

-continued

```
gatatcccgt tagaagaacc agaagtaaaa gtaatcccag atgacaacca gacggacagt   3780
ggtatggttc ttgcctcaga agagctgaaa actttggaag acagaaccaa attatctcca   3840
tcttttggtg gaatggtgcc cagcaaaagc agggagtctg tggcatctga aggctcaaac   3900
cagacaagcg gctaccagtc cggatatcac tccgatgaca cagacaccac cgtgtactcc   3960
agtgaggaag cagaactttt aaagctgata gagattggag tgcaaaccgg tagcacagcc   4020
cagattctcc agcctgactc ggggaccaca ctgagctctc ctcctgttta a            4071
```